US007562872B2

(12) United States Patent
Okada

(10) Patent No.: US 7,562,872 B2
(45) Date of Patent: Jul. 21, 2009

(54) GAMING MACHINE

(75) Inventor: Kazuo Okada, Koto-ku (JP)

(73) Assignee: Aruze Corp., Tokyo (JP)

( * ) Notice: Subject to any disclaimer, the term of this patent is extended or adjusted under 35 U.S.C. 154(b) by 457 days.

(21) Appl. No.: 11/334,426

(22) Filed: Jan. 19, 2006

(65) Prior Publication Data

US 2006/0189392 A1 Aug. 24, 2006

(30) Foreign Application Priority Data

Jan. 26, 2005 (JP) ............................. 2005-018519
Jan. 28, 2005 (JP) ............................. 2005-021068

(51) Int. Cl.
*A61F 7/02* (2006.01)

(52) U.S. Cl. ................ 273/108; 273/118 R; 273/121 R

(58) Field of Classification Search ............. 273/121 R, 273/121 A, 121 B, 118 R, 118 A, 108; 463/46; D21/324; 312/223.1
See application file for complete search history.

(56) References Cited

U.S. PATENT DOCUMENTS

| | | | | |
|---|---|---|---|---|
| 2,584,917 A | | 2/1952 | Powell | |
| 4,625,974 A | * | 12/1986 | Andrews | 273/407 |
| 4,647,043 A | * | 3/1987 | Wiczer | 273/121 R |
| 4,854,047 A | | 8/1989 | Conanan | |
| 4,865,322 A | * | 9/1989 | Krutsch | 273/121 R |
| 5,710,415 A | | 1/1998 | Kono et al. | |
| 7,063,295 B2 | * | 6/2006 | Kwon | 248/276.1 |
| 2003/0042671 A1 | * | 3/2003 | Houston, Jr. | 273/118 R |
| 2004/0083616 A1 | | 5/2004 | Hamar | |

FOREIGN PATENT DOCUMENTS

| | | | | |
|---|---|---|---|---|
| CN | 2215716 Y | | 12/1995 |
| CN | 1139784 A | | 1/1997 |
| DE | G 94 11 422.6 | | 12/1994 |
| EP | 1 498 860 A1 | | 1/2005 |
| FR | 2 847 035 | | 5/2004 |
| JP | 10-234997 | | 9/1998 |
| JP | 11-70261 | | 3/1999 |
| JP | 2000-88570 | | 3/2000 |
| JP | 2002-35393 | | 2/2002 |
| JP | 2002177608 A | * | 6/2002 |
| JP | 2002-346032 | | 12/2002 |
| JP | 2004033251 A | * | 2/2004 |
| JP | 2005-10129 | | 1/2005 |
| JP | 2005046231 A | * | 2/2005 |
| JP | 2005329168 A | * | 12/2005 |
| JP | 2005342181 A | * | 12/2005 |

OTHER PUBLICATIONS

U.S. Appl. No. 11/328,281, filed Jan. 10, 2006, Okada.
U.S. Appl. No. 11/334,426, filed Jan. 19, 2006, Okada.

* cited by examiner

*Primary Examiner*—Raleigh W. Chiu
(74) *Attorney, Agent, or Firm*—Oblon, Spivak, McClelland, Maier & Neustadt, P.C.

(57) ABSTRACT

A gaming machine includes a cabinet, a lower liquid crystal display, a manual adjustment mechanism and liquid storage portions. The lower liquid crystal display is attached to the cabinet. The manual adjustment mechanism adjusts an attachment angle of the lower liquid crystal display with respect to the cabinet, in accordance with a movement of the lower liquid crystal display. The liquid storage portion has liquid and a plurality of inclination indicators. The attachment angle is presented based on a relative positional relation between the liquid and the inclination indicators.

9 Claims, 25 Drawing Sheets

FIG. 10

FIRST REEL BAND (101)

| CODE NO. | PATTERN |
|---|---|
| 00 | J |
| 01 | Q |
| 02 | WILD |
| 03 | J |
| 04 | Q |
| 05 | CRAB |
| 06 | A |
| 07 | WORM |
| 08 | K |
| 09 | FISH |
| 10 | PUNK |
| 11 | Q |
| 12 | SHARK |
| 13 | CRAB |
| 14 | K |
| 15 | A |
| 16 | OCTOPUS |
| 17 | J |
| 18 | Q |
| 19 | FISH |
| 20 | K |
| 21 | J |
| 22 | SARDINE |
| 23 | CRAB |
| 24 | J |
| 25 | WORM |
| 26 | Q |
| 27 | CRAB |
| 28 | A |
| 29 | FISH |

SECOND REEL BAND (102)

| CODE NO. | PATTERN |
|---|---|
| 00 | OCTOPUS |
| 01 | A |
| 02 | WILD |
| 03 | OCTOPUS |
| 04 | K |
| 05 | J |
| 06 | FISH |
| 07 | WORM |
| 08 | J |
| 09 | CRAB |
| 10 | OCTOPUS |
| 11 | A |
| 12 | SARDINE |
| 13 | WORM |
| 14 | J |
| 15 | OCTOPUS |
| 16 | SHARK |
| 17 | J |
| 18 | OCTOPUS |
| 19 | CRAB |
| 20 | Q |
| 21 | PUNK |
| 22 | CRAB |
| 23 | OCTOPUS |
| 24 | J |
| 25 | WORM |
| 26 | CRAB |
| 27 | K |
| 28 | OCTOPUS |
| 29 | WORM |

THIRD REEL BAND (103)

| CODE NO. | PATTERN |
|---|---|
| 00 | A |
| 01 | K |
| 02 | WILD |
| 03 | WORM |
| 04 | Q |
| 05 | WILD |
| 06 | PUNK |
| 07 | A |
| 08 | J |
| 09 | SARDINE |
| 10 | A |
| 11 | Q |
| 12 | WORM |
| 13 | K |
| 14 | FISH |
| 15 | Q |
| 16 | CRAB |
| 17 | A |
| 18 | K |
| 19 | SHARK |
| 20 | Q |
| 21 | K |
| 22 | OCTOPUS |
| 23 | Q |
| 24 | A |
| 25 | WORM |
| 26 | J |
| 27 | Q |
| 28 | PUNK |
| 29 | K |

FOURTH REEL BAND (104)

| CODE NO. | PATTERN |
|---|---|
| 00 | Q |
| 01 | J |
| 02 | WILD |
| 03 | Q |
| 04 | K |
| 05 | WILD |
| 06 | A |
| 07 | K |
| 08 | SARDINE |
| 09 | A |
| 10 | K |
| 11 | CRAB |
| 12 | PUNK |
| 13 | K |
| 14 | SHARK |
| 15 | WORM |
| 16 | A |
| 17 | OCTOPUS |
| 18 | FISH |
| 19 | K |
| 20 | WORM |
| 21 | PUNK |
| 22 | A |
| 23 | FISH |
| 24 | CRAB |
| 25 | K |
| 26 | Q |
| 27 | OCTOPUS |
| 28 | WORM |
| 29 | Q |

FIFTH REEL BAND (105)

| CODE NO. | PATTERN |
|---|---|
| 00 | J |
| 01 | A |
| 02 | WILD |
| 03 | J |
| 04 | A |
| 05 | FISH |
| 06 | CRAB |
| 07 | PUNK |
| 08 | K |
| 09 | SARDINE |
| 10 | Q |
| 11 | CRAB |
| 12 | K |
| 13 | WORM |
| 14 | FISH |
| 15 | J |
| 16 | OCTOPUS |
| 17 | Q |
| 18 | WORM |
| 19 | J |
| 20 | Q |
| 21 | OCTOPUS |
| 22 | A |
| 23 | PUNK |
| 24 | WORM |
| 25 | Q |
| 26 | CRAB |
| 27 | PUNK |
| 28 | K |
| 29 | OCTOPUS |

FIG. 11

| | 2K | 3K | 4K | 5K | |
|---|---|---|---|---|---|
| WILD | 10 | 320 | 2500 | 6000 | Left → Right/SUBSTITUTE |
| SHARK | 3 | 25 | 150 | 1000 | Left → Right |
| FISH | 2 | 15 | 120 | 500 | Left → Right |
| PUNK | 2 | 10 | 120 | 400 | Left → Right |
| OCTOPUS | 2 | 8 | 50 | 300 | Left → Right |
| CRAB | | 7 | 50 | 200 | Left → Right |
| WORM | | 6 | 40 | 150 | Left → Right |
| A | | 5 | 25 | 120 | Left → Right |
| K | | 5 | 25 | 120 | Left → Right |
| Q | | 5 | 20 | 100 | Left → Right |
| J | | 5 | 20 | 100 | Left → Right |
| SARDINE | 2 | 5 | 10 | 125 | SCATTER/Trigger |

GAMING MACHINE

CROSS REFERENCE TO RELATED APPLICATION

This application claims benefit of priority under 35 U.S.C. § 119 to Japanese Patent Application No. 2005-018519, filed on Jan. 26, 2005 and No. 2005-021068 filed on Jan. 28, 2005, the entire contents of which are incorporated by reference herein.

BACKGROUND OF THE INVENTION

1. Field of the Invention

The present invention relates to a gaming machine configured to display a level of an inclination of a display apparatus.

2. Description of the Related Art

A pachinko gaming machine has been known as a gaming machine including an inclination display tool for displaying a level of an inclination of the gaming machine. The inclination of the pachinko gaming machine has a large influence on a movement of a pachinko ball. This raises a demand that managers and/or players in gaming halls want to check the level of the inclination of the pachinko gaming machine in an easy manner.

A conventional inclination display tool is disclosed in Japanese Patent Laid-open Publication No. 10-234997. The inclination display tool is provided at an outer frame or a lower ball tray of a pachinko gaming machine. A manager and/or a player can visually check the level of the inclination of the pachinko gaming machine via the inclination display tool. However, the inclination display tool uses a level vial for construction tool. This requires the manager and/or the player to read carefully a displaced position of a bubble in the level vial in order to check visually the level of the inclination of the pachinko gaming machine. Especially, the bubble indicates a plurality of graduations in the level vial because the bubble has a predetermined width so as to be visually recognized by the manager and/or the player in an easy manner. This leads to difficulty of checking work.

On the other hand, in another gaming machine including a display apparatus for displaying game contents, the display apparatus capable of being adjusted to a desired angle manually has been developed so that the game contents can be easily seen. With the advent of this gaming machine, there is another demand that managers and/or players in gaming halls want to check the level of the inclination of the display apparatus in an easy manner.

SUMMARY OF THE INVENTION

It is an object of the present invention to provide a gaming machine capable of presenting a level of an inclination of a display apparatus such that the level can be read easily.

In order to achieve the object, the present invention provides a gaming machine comprising: a cabinet; a display apparatus attached to the cabinet; an adjustment unit configured to adjust an attachment angle of the display apparatus with respect to the cabinet, in accordance with a movement of the display apparatus; and a liquid storage unit having liquid and a plurality of inclination indicators and configured to present the attachment angle based on a relative positional relation between the liquid and the inclination indicators.

According to the present invention, a manager and/or a player in a gaming hall can easily check the attachment angle of the display apparatus via the liquid storage unit from the front face of the gaming machine, based on the relative positional relation between the liquid level of the liquid and the inclination indicators.

In order to achieve the object, the present invention provides a gaming machine comprising: a cabinet; a display apparatus attached to the cabinet; an adjustment unit configured to adjust an attachment angle of the display apparatus with respect to the cabinet, in accordance with a movement of the display apparatus; a detector configured to detect the attachment angle; and a display control unit configured to display the attachment angle detected by the detector on the display apparatus.

According to the present invention, a manager and/or a player in a gaming hall can easily check the attachment angle of the display apparatus on which the display control unit displays the attachment angle from the front face of the gaming machine.

BRIEF DESCRIPTION OF THE DRAWINGS

FIG. 10 is an explanatory diagram of symbol columns variably displayed in respective variable display portions in the first embodiment of the present invention.

FIG. 11 is an explanatory diagram of winning combinations and dividends to the winning combinations in the first embodiment of the present invention.

DESCRIPTION OF THE PREFERRED EMBODIMENTS

Hereinafter, the first and second embodiments of the present invention will be described with reference to FIGS. 1 to 29.

First Embodiment

Figure 1:
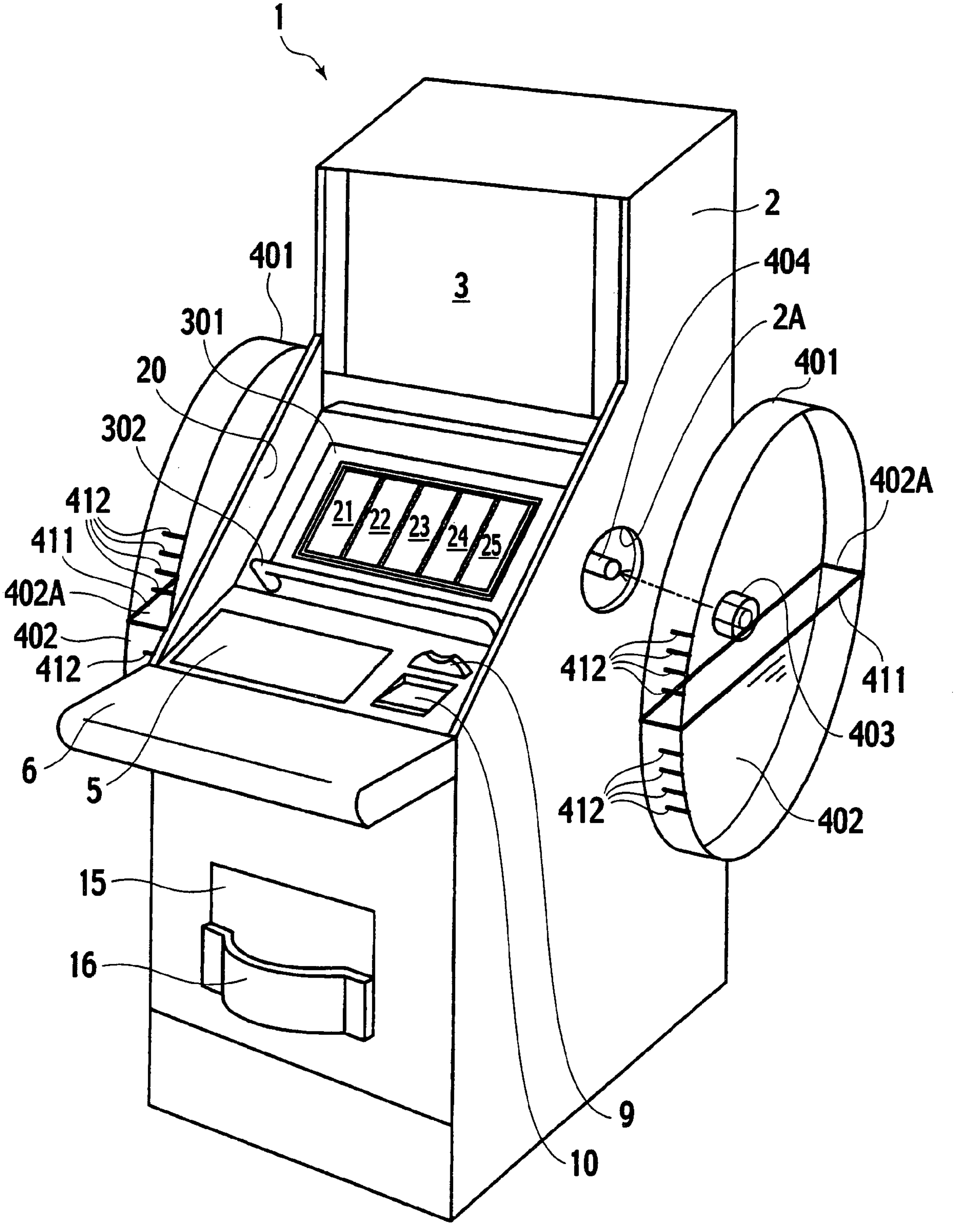
FIG. 1 is a perspective view of a slot machine in a first embodiment of the present invention.
Figure 2:
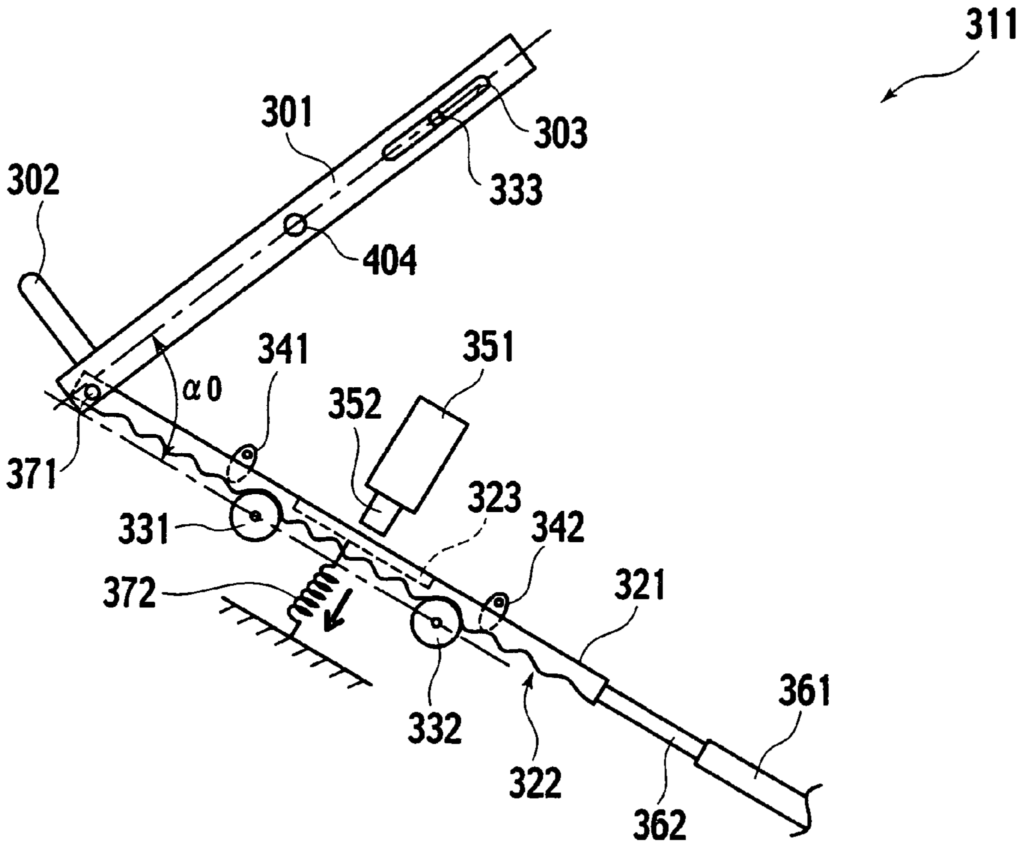
FIG. 2 is a schematic side view of a manual adjustment mechanism when an attachment angle of a lower liquid crystal display is a default angle in the first embodiment of the present invention.

As shown in FIG. 1, a gaming machine (slot machine in this embodiment) 1 comprises a cabinet 2, an upper liquid crystal display 3, an operation table 5, an arm rest 6, a coin insertion slot 9, a bill insertion slot 10, a coin payout slot 15, a coin receiving portion 16, a machine front face panel 20, a lower liquid crystal display 301, a grip 302, a manual adjustment mechanism 311 and liquid storage portions 401, 401.

The cabinet 2 is a slant type cabinet which makes a player sit on a chair to play a slot game and forms the entirety of the slot machine 1. The upper liquid crystal display 3 is provided at an upper part of a front face of the cabinet 2. The upper liquid crystal display 3 displays information for a gaming method, types of winning combinations, dividends to the winning combinations and game effects or the like. The machine front face panel 20 is provided at a center of the front face of the cabinet 2.

The lower liquid crystal display 301 is provided at a center of the machine front face panel 20. The lower liquid crystal display 301 displays a credit and has variable display portions 21, 22, 23, 24, 25. The slot machine 1 rotates or stops a video reel so that the respective variable display portions 21, 22, 23, 24, 25 provide a variable display or a stop-display of a plurality of symbols (three symbols in this embodiment), thereby promoting the slot game.

The slot game has a general mode and a bonus mode. In the general mode, when a player performs a betting operation based on the number of credits owned by the player, the slot machine 1 provides the variable display or the stop-display of the plurality of symbols and then performs a predetermined processing (e.g., payout processing or a processing for switching to a bonus mode) in accordance with a combination of symbols of the stop-display. In the bonus mode, the player can automatically and continuously perform a plurality of the slot games (e.g., 15 to 25 games) in accordance with a sortition result at the time of switching to the bonus mode, without betting the credit or the like.

Figure 12:
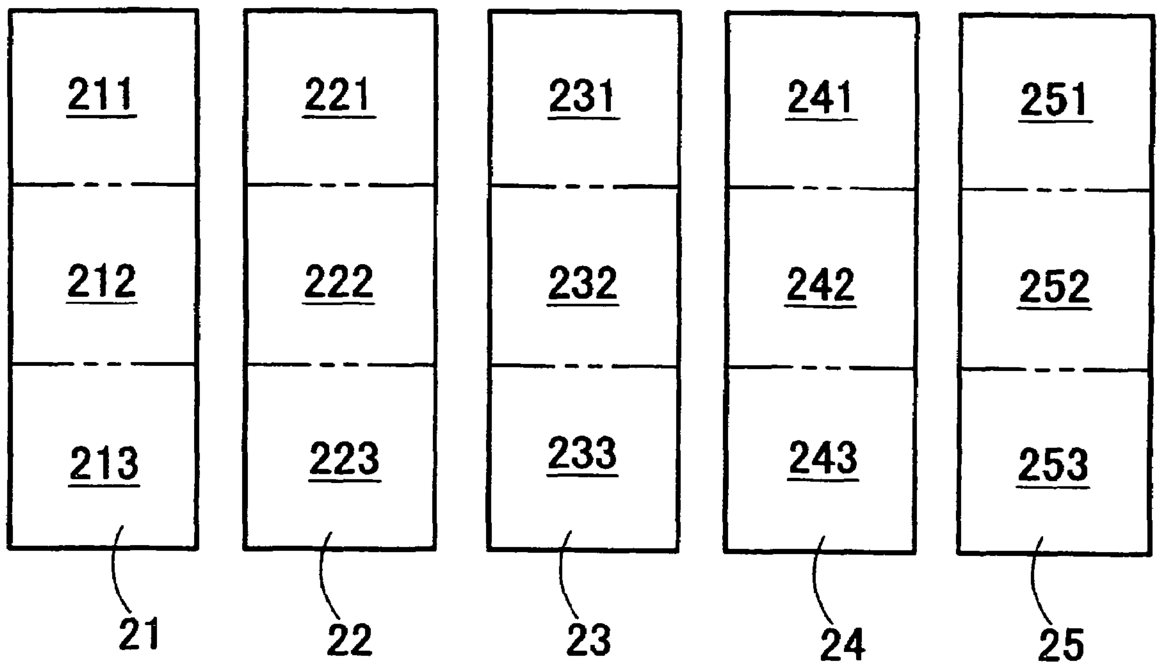
FIG. 12 is a diagram of stop-display regions of five variable display portions in the first embodiment of the present invention.

The respective variable display portions 21, 22, 23, 24, 25 provide the stop-display of three symbols. Specifically, as shown in FIG. 12, the variable display portion 21 (22, 23, 24 or 25) is divided to a first stop-display region 211 (221, 231, 241 or 251), a second stop-display region 212 (222, 232, 242 or 252) and a third stop-display region 213 (223, 233, 243 or 253). The three symbols are stop-displayed at three stop-display regions of each variable display portion, respectively.

The slot game has twenty-five paylines formed by five stop-display regions selected among the first stop-display regions 211, 221, 231, 241, 251, the second stop-display regions 212, 222, 232, 242, 252 and the third stop-display region 213, 223, 233, 243, 253. A payline validated among the twenty-five paylines is called a validated payline. In the validated payline, when specific five symbols in a specific mode are stop-displayed in the corresponding five stop-display regions, respectively, a dividend is paid to the player.

Next, five symbol columns variably displayed in the variable display portions 21, 22, 23, 24, 25 in the general mode will be described. As shown in FIG. 10, symbol columns of a first reel band 101, a second reel band 102, a third reel band 103, a fourth reel band 104 and a fifth reel band 105 are variably displayed in the variable display portions 21, 22, 23, 24, 25, respectively. The symbol columns of the respective reel bands are arranged by combining a plurality of symbols so that neighbor symbols are different to each other. More specifically, the symbol columns of the respective reel bands are comprised of thirty symbols which is arranged by appropriately combining twelve symbols of "WILD", "SHARK", "FISH", "PUNK", "OCTOPUS", "CRAB", "WORM", "A", "K", "Q", "J" and "SARDINE" so that neighbor symbols are different to each other.

The "SHARK", "FISH", "PUNK", "OCTOPUS", "CRAB", "WORM" and "SARDINE" show the symbols of a shark, a fish, a person holding a guitar, an octopus, a crab, a worm and a sardine, respectively (not shown). The "WILD", "A", "K", "Q" and "J" show alphabet symbols, respectively.

The "SARDINE" is a scatter symbol for switching the general mode to the bonus mode. More specifically, when three or more "SARDINEs" are stop-displayed on three variable display portions independent from the validated paylines, the current mode is switched to the bonus mode. Although the "WILD" can be substituted as a symbol representing "SHARK", "FISH", "PUNK", "OCTOPUS", "CRAB", "WORM", "A", "K", "Q" or "J", it cannot be substituted as a symbol representing "SARDINE".

When the symbol columns of the first reel band 101, the second reel band 102, the third reel band 103, the fourth reel band 104 and the fifth reel band 105 are stop-displayed at the variable display portions 21, 22, 23, 24, 25, respectively, three symbols of each reel band are stop-displayed at three stop-regions of a corresponding variable display portion, respectively. Winning combinations are previously determined based on combinations of symbols. When the combination of symbols corresponding to one of the winning combinations is stop-displayed on the validated paylines, a dividend to the winning combination is added to the credit as well as a conventional slot machine.

Figure 7:
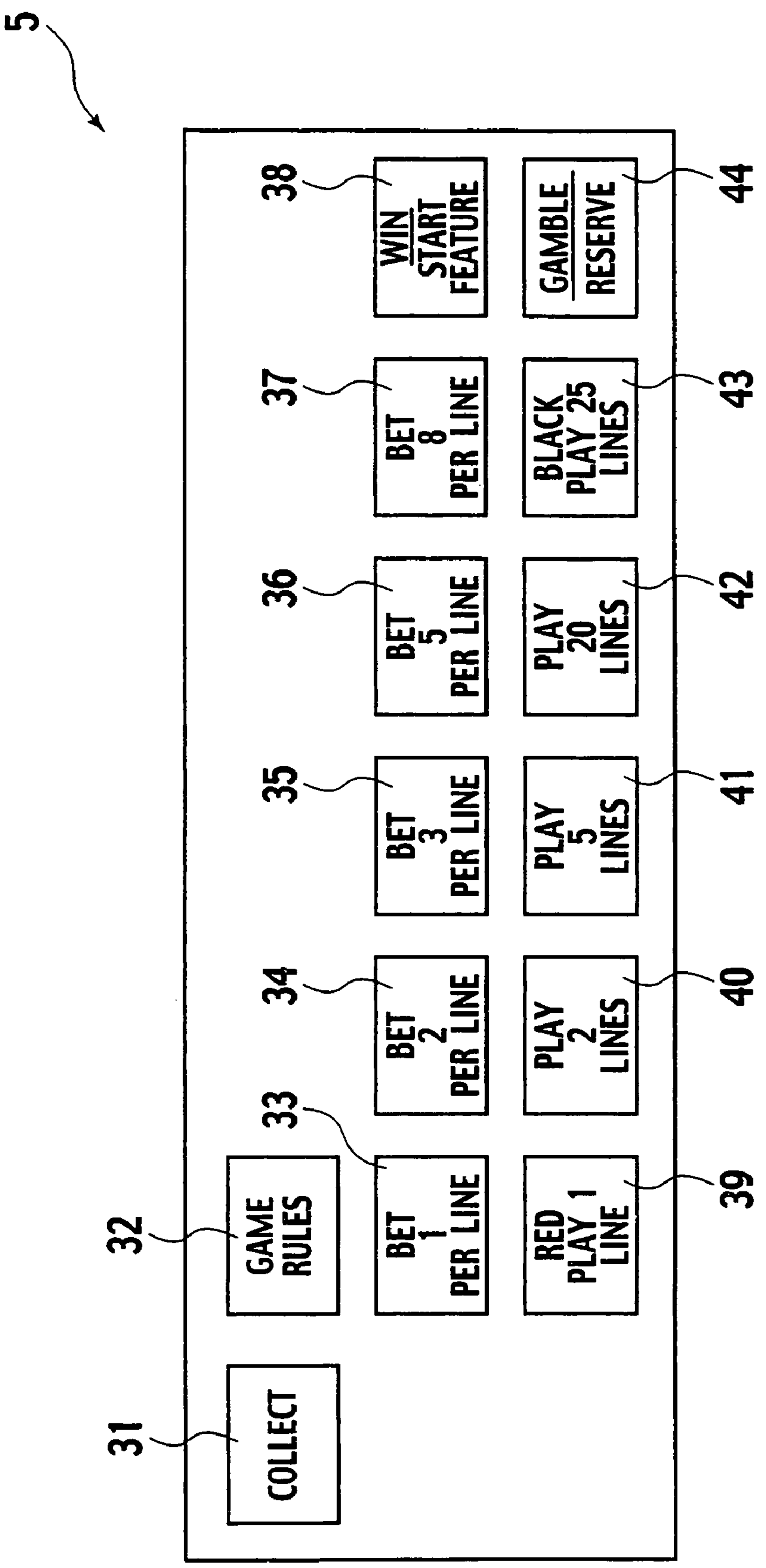
FIG. 7 is a front view of an operation table in the first embodiment of the present invention.

As shown in FIG. 1, the operation table 5 is provided at a left side of a lower part of the front face of the cabinet 2. As shown in FIG. 7, the operation table 5 has a COLLECT button 31, a GAME RULES button 32, a BET1 PER LINE button 33, a BET2 PER LINE button 34, a BET3 PER LINE button 35, a BET 5 PER LINE button 36, a BET8 PER LINE button 37, a WIN START FEATURE button 38, a RED PLAY1 LINE button 39, a PLAY2 LINES button 40, a PLAY5 LINES button 41, a PLAY20 LINES button 42, a BLACK PLAY25 LINES button 43 and a GAMBLE RESERVE button 44.

The COLLECT button 31 and the GAME RULES button 32 are provided at an upper stage of the operation table 5 from a left side in this order. The BET1 PER LINE button 33, the BET2 PER LINE button 34, the BET3 PER LINE button 35, the BET 5 PER LINE button 36, the BET8 PER LINE button 37 and the WIN START FEATURE button 38 are provided at a middle stage of the operation table 5 from the left side in this order. The RED PLAY1 LINE button 39, the PLAY2 LINES button 40, the PLAY5 LINES button 41, the PLAY20 LINES button 42, the BLACK PLAY25 LINES button 43 and the GAMBLE RESERVE button 44 are provided at a lower stage of the operation table 5 from the left side in this order.

The COLLECT button 31 is depressed by the player when the player stops the general mode. When the player depresses the COLLECT button 31, the slot machine 1 pays out to the coin receiving portion 16 coins equivalent to the number of credits obtained in the slot game, through the coin payout slot 15. The COLLECT button 31 is attached with a COLLECT switch 45. When the player depresses the COLLECT button 31, the COLLECT switch 45 outputs a switch signal to a CPU 50 (see FIG. 8).

The GAME RULES button 32 is depressed by the player when the player does not know an operating procedure of the slot game or the like. When the player depresses the GAME RULES button 32, the upper liquid crystal display 3 (or the lower liquid crystal display 301) displays help information. The GAME RULES button 32 is attached with a GAME RULES switch 46. When the player depresses the GAME RULES button 32, the GAME RULES switch 46 outputs a switch signal to the CPU 50 (see FIG. 8).

The BET1 PER LINE button 33 is depressed by the player when the player performs one bet to each validated payline. When the player depresses the BET1 PER LINE button 33, the BET1 PER LINE button 33 outputs a switch signal to the CPU 50 via a 1-BET switch 57 attached to the BET1 PER LINE button 33 (see FIG. 8). The BET2 PER LINE button 34 is depressed by the player when the player performs two bets to each validated payline. When the player depresses the BET2 PER LINE button 34, the BET2 PER LINE button 34 outputs a switch signal to the CPU 50 via a 2-BET switch 58 attached to the BET2 PER LINE button 34 (see FIG. 8).

The BET3 PER LINE button 35 is depressed by the player when the player performs three bets to each validated payline. When the player depresses the BET3 PER LINE button 35, the BET3 PER LINE button 35 outputs a switch signal to the CPU 50 via a 3-BET switch 59 attached to the BET3 PER LINE button 35 (see FIG. 8). The BET5 PER LINE button 36 is depressed by the player when the player performs five bets to each validated payline. When the player depresses the BET5 PER LINE button 36, the BET5 PER LINE button 36 outputs a switch signal to the CPU 50 via a 5-BET switch 60 attached to the BET5 PER LINE button 36 (see FIG. 8).

The BET8 PER LINE button 37 is depressed by the player when the player performs eight bets to each validated payline. When the player depresses the BET8 PER LINE button 37, the BET8 PER LINE button 37 outputs a switch signal to the CPU 50 via an 8-BET switch 61 attached to the BET8 PER LINE button 37 (see FIG. 8). Thus, the depression of the BET1 PER LINE button 33, the BET2 PER LINE button 34, the BET3 PER LINE button 35, the BET5 PER LINE button 36 or the BET8 PER LINE button 37 determines the number of bets to each validated payline.

The WIN START FEATURE button 38 is depressed by the player when the player starts the bonus mode or adds the dividend obtained in the bonus mode to the credit. When the player depresses the WIN START FEATURE button 38, the WIN START FEATURE button 38 outputs a switch signal to the CPU 50 via a WIN/START switch 47 attached to the WIN START FEATURE button 38 (see FIG. 8).

The RED PLAY1 LINE button 39 is depressed by the player when the player starts the slot game by specifying the number of validated paylines as “1”. When the player depresses the RED PLAY1 LINE button 39, the RED PLAY1 LINE button 39 outputs a switch signal to the CPU 50 via a 1-LINE switch 62 attached to the RED PLAY1 LINE button 39 (see FIG. 8). The PLAY2 LINES button 40 is depressed by the player when the player starts the slot game by specifying the number of validated paylines as “2”. When the player depresses the PLAY2 LINES button 40, the PLAY2 LINES button 40 outputs a switch signal to the CPU 50 via a 2-LINES switch 63 attached to the PLAY2 LINES button 40 (see FIG. 8).

The PLAY5 LINES button 41 is depressed by the player when the player starts the slot game by specifying the number of validated paylines as “5”. When the player depresses the PLAY5 LINES button 41, the PLAY5 LINES button 41 outputs a switch signal to the CPU 50 via a 5-LINES switch 64 attached to the PLAY5 LINES button 41 (see FIG. 8). The PLAY20 LINES button 42 is depressed by the player when the player starts the slot game by specifying the number of validated paylines as “20”. When the player depresses the PLAY20 LINES button 42, the PLAY20 LINES button 42 outputs a switch signal to the CPU 50 via a 20-LINES switch 65 attached to the PLAY20 LINES button 42 (see FIG. 8).

The BLACK PLAY25 LINES button 43 is depressed by the player when the player starts the slot game by specifying the number of validated paylines as “25”. When player depresses the BLACK PLAY25 LINES button 43, the BLACK PLAY25 LINES button 43 outputs a switch signal to the CPU 50 via a 25-LINES switch 66 attached to the BLACK PLAY25 LINES button 43 (see FIG. 8).

When the player depresses the RED PLAY1 LINE button 39, the PLAY2 LINES button 40, the PLAY5 LINES button 41, the PLAY20 LINES button 42 or the BLACK PLAY25 LINES button 43, the number of validated paylines is determined and then the variable display portions 21, 22, 23, 24, 25 of the lower liquid crystal display 301 variably display a plurality of symbols. It is noted that the RED PLAY1 LINE button 39 or the BLACK PLAY25 LINES button 43 is also used when red or black is selected in a double down mode performed by using the credit obtained in the bonus mode.

The GAMBLE RESERVE button 44 is depressed by the player when the player is temporarily away from the seat or when the player switches the bonus mode to the double down mode after the bonus mode is completed. When the player depresses the GAMBLE RESERVE button 44, the GAMBLE RESERVE button 44 outputs a switch signal to the CPU 50 via a GAMBLE RESERVE switch 48 attached to the GAMBLE RESERVE button 44 (see FIG. 8).

As shown in FIG. 1, the armrest 6 is provided in a protruded manner from the lower part of the front face of the cabinet 2 to a front part of the slot machine 1. The coin insertion slot 9 and the bill insertion slot 10 are provided at a right side of the lower part of the front face of the cabinet 2.

Figure 8:
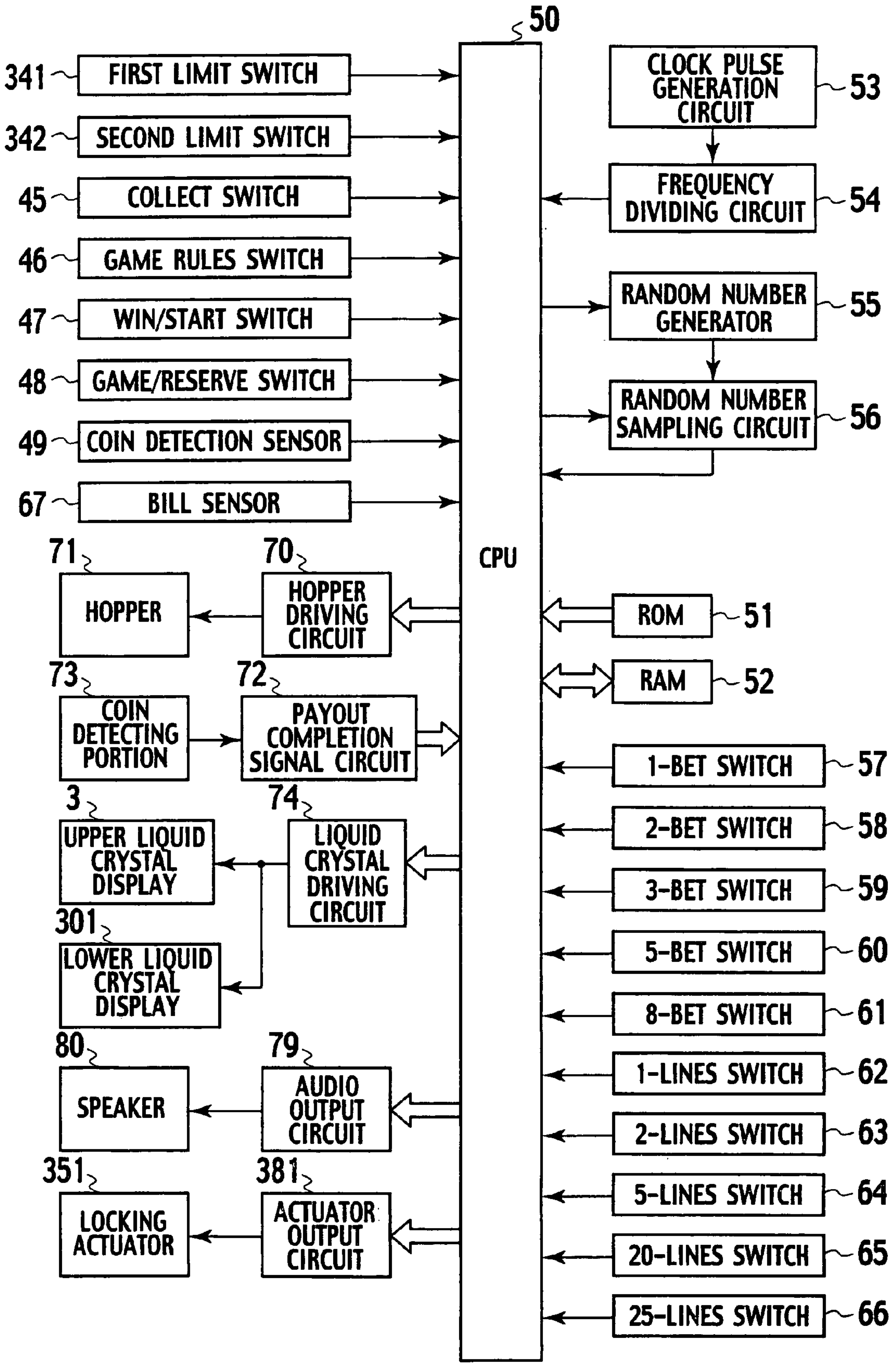
FIG. 8 is a control block diagram of the slot machine in the first embodiment of the present invention.

When the player inserts a coin into the coin insertion slot 9, the coin insertion slot 9 outputs a coin detection signal to the CPU 50 via a coin detection sensor 49 (see FIG. 8). When the CPU 50 receives the coin detection signal, the CPU 50 adds the credit equivalent to the value of the inserted coin to the credit of the player.

When the player inserts a bill to the bill insertion slot 10, the bill insertion slot 10 outputs a bill detection signal to the CPU 50 via an inserted-bill sensor 67 (see FIG. 8). When the CPU 50 receives the bill detection signal, the CPU 50 adds the credit equivalent to the value of the inserted bill to the credit of the player.

The coin payout slot 15 is provided at the lower part of the cabinet 2. The coin receiving portion 16 extends from the coin payout slot 15 and receives a coin paid out from the coin payout slot 15. A coin detecting portion 73 is attached to an interior of the coin payout slot 15 and detects the number of coins paid out from the coin payout slot 15.

The grip 302 is provided at a lower part of the lower liquid crystal display 302. When the player grips the grip 302 and then moves the lower liquid crystal display 302, an inclination (attachment angle) of the lower liquid crystal display 301 with respect to the cabinet 2 is manually adjusted with multiple levels.

As shown in FIGS. 2 to 6, the manual adjustment mechanism 311 comprises a support base 321, a wave-like portion 322, a lock plate 323, a pair of first rollers 331, 331, a pair of second rollers 332, 332, a pair of protrusion portions 333, 333, a first limit switch 341, a second limit switch 342, a locking actuator 351, a stopper 361, a pair of turning pins 371, 371, a biasing spring 372 and a pair of shafts 404, 404.

Figure 3:
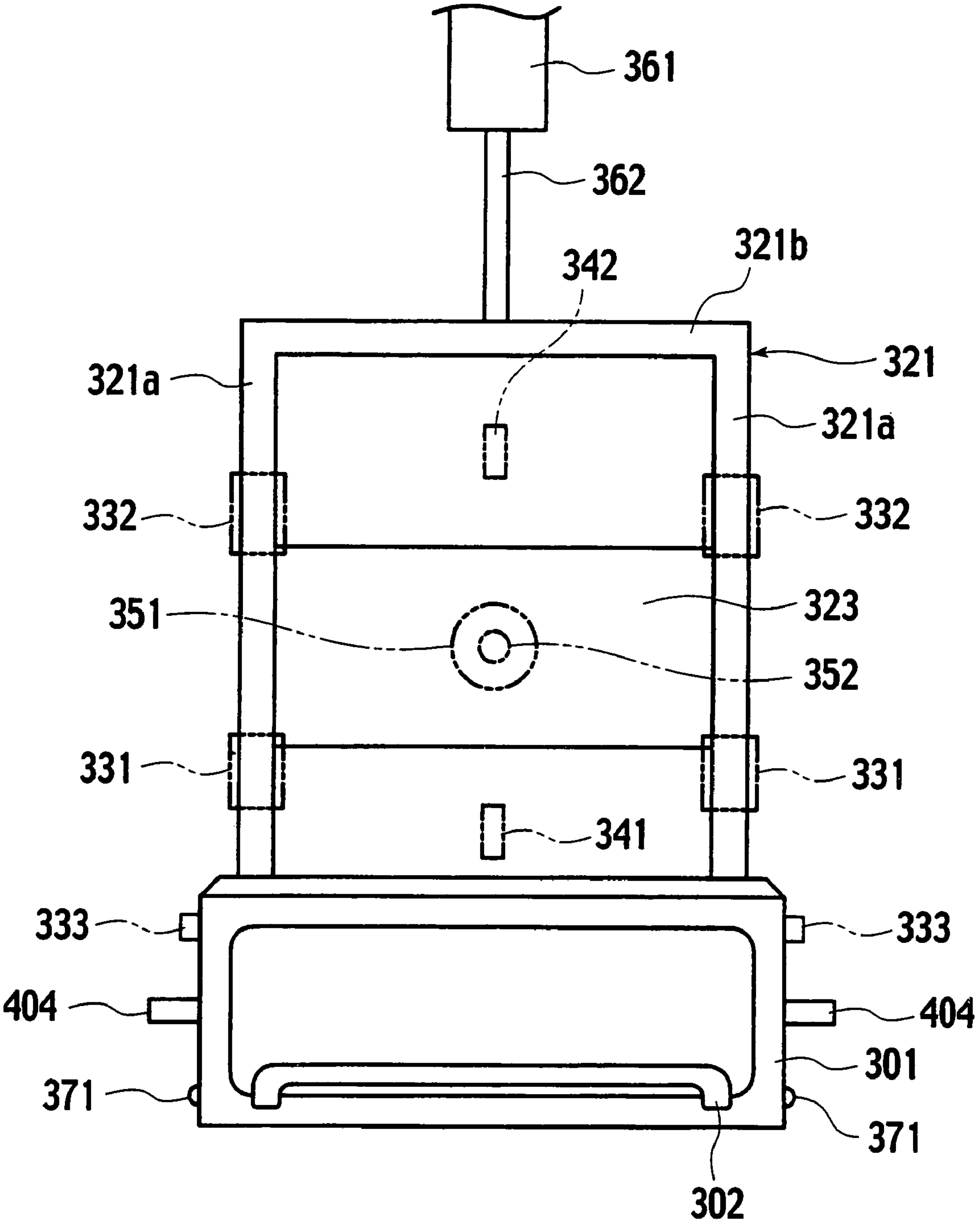
FIG. 3 is a schematic plan view of the manual adjustment mechanism in the first embodiment of the present invention.
Figure 4:
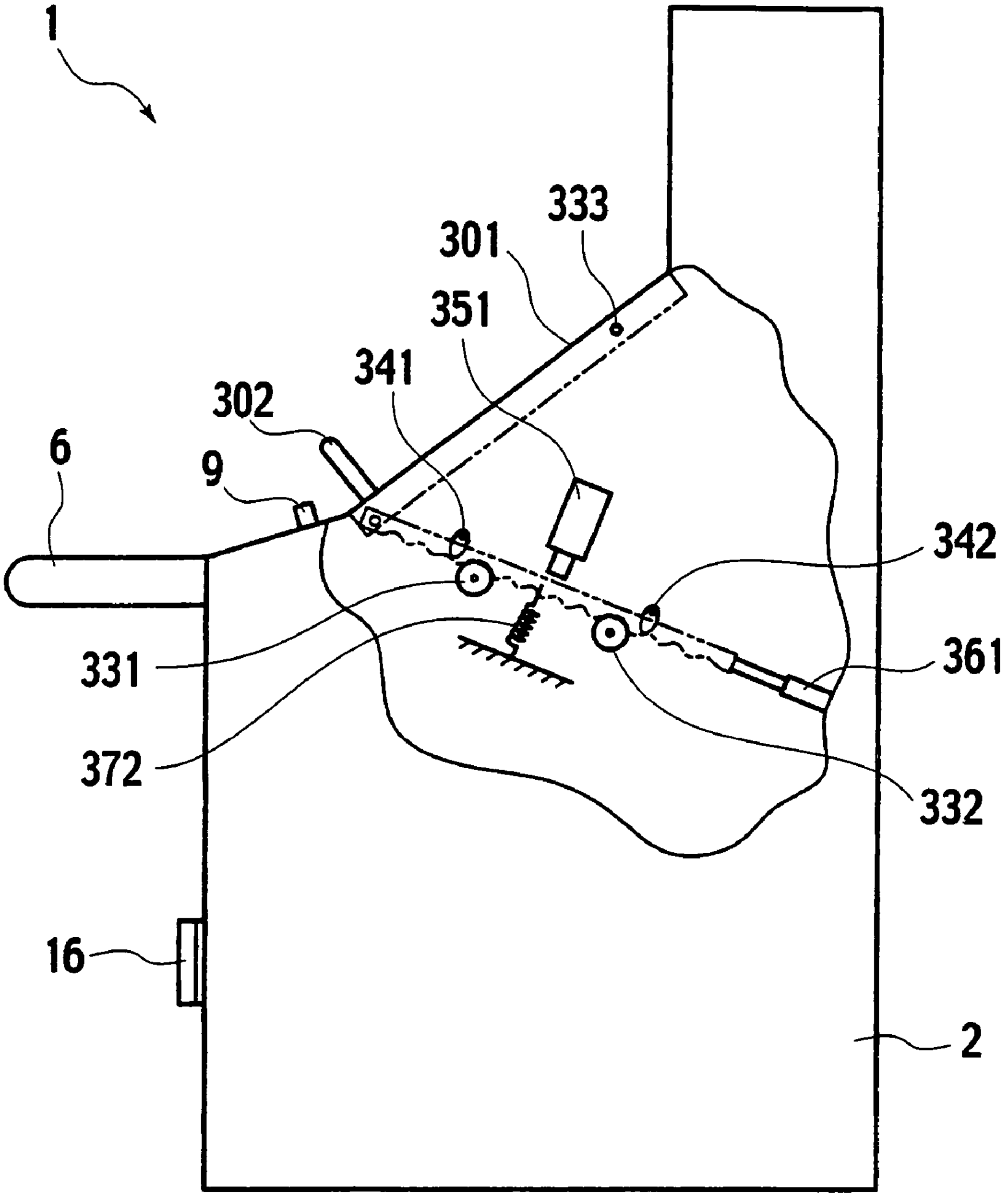
FIG. 4 is a schematic side view of the manual adjustment mechanism in the first embodiment of the present invention.

As shown in FIG. 3, the support base 321 is formed to be a substantially U-like shape and provided with arm portions **321*a*, 321*a* and a connection portion 321*b*. The arm portion 321*a* has one end integrally connected to an end part of the connection portion 321*b* and the other end rotatably supported at the lower part of the lower liquid crystal display 302 via the turning pin 371. The wave-like portion 322 is disposed at bottom faces of the arm portions 321*a*, 321*a* of the support base 321 (see FIG. 2). The lock plate 323 is fixed at a center part of the arm portions 321*a*, 321*a* of the support base 321 so as to be parallel with the connection portion 321*b* of the support base 321**.

The first rollers 331, 331 are mounted on the cabinet 2 and are placed on the support base 321 via the wave-like portion 322. The second rollers 332, 332 are mounted on the cabinet 2 and are placed on the support base 321 via the wave-like portion 322. The protrusion portions 333, 333 are mounted on the cabinet 2 and are inserted to guide grooves 303, 303 formed on both side faces of the lower liquid crystal display 301. The protrusion portions 333, 333 regulate the movement of the lower liquid crystal display 301. The first limit switch 341 is mounted on the cabinet 2 so as to be positioned at a hollow portion of the support base 321 at one end side of the arm portion **321*a* when the inclination (attachment angle) of the lower liquid crystal display 302 with respect to the cabinet 2 is a default angle α0 (see FIG. 2). The second limit switch 342 is mounted on the cabinet 2 so as to be positioned at the hollow portion of the support base 321 at the other end side of the arm portion 321*a* when the inclination (attachment angle) of the lower liquid crystal display 302 with respect to the cabinet 2 is the default angle α0 (see FIG. 2**).

The first rollers 331, 331 and the second rollers 332, 332 are mounted on the cabinet 2. Thus, an angle formed by the intersection of a center line passing the support points of the first roller 331 and the second roller 332 with a center line of the lower liquid crystal display 301 is defined as the inclination (attachment angle) of the lower liquid crystal display 301 with respect to the cabinet 2.

When the lock plate 323 contacts with the first limit switch 341 in accordance with the movement of the support base 321, the first limit switch 341 transmits a detection signal to the CPU 50. Similarly, when the lock plate 323 contacts with the second limit switch 342 in accordance with the movement of the support base 321, the second limit switch 342 transmits a detection signal to the CPU 50.

The locking actuator 351 is mounted on the cabinet 2 so as to be positioned on an upper side of the lock plate 323. When the CPU 50 detects the detection signal from the first limit switch 341 or the second limit switch 342, the CPU 50 operates the locking actuator 351 so that a rod 352 of the locking actuator 351 pushes the lock plate 323 toward the biasing spring 371. The stopper 361 is mounted on the cabinet 2 and has a rod 362 fixed at a center of the connection portion **321*b* of the support base 321** in a retractable manner.

The biasing spring 372 has one end fixed to the cabinet 2 and the other end fixed at a center part of the lock plate 323. The biasing spring 372 always compresses the support base 321 toward the first rollers 331, 331 and the second rollers 332, 332. Thus, upper parts of the first rollers 331, 331 and the second rollers 332, 332 are held in concave portions of the wave-like portions 322 of the support base 321. As a result, the attachment angle of the lower liquid crystal display 301 which is rotatably supported by the support base 321 is retained.

The shafts 404, 404 are provided at the both side faces of the lower liquid crystal display 301 in a protruded manner to be exposed via penetration holes 2A, 2A formed at both side faces of the cabinet 2.

The liquid storage portions 401, 401 are made of a columnar transparent plastic which has a hollow portion therein and are mounted on the both side faces of the cabinet 2, respectively. The liquid storage portion 401 comprises liquid 402, a support portion 403, a first inclination indicator 411 and a plurality of second inclination indicators 412. The liquid 402 is colored by fluorescent paint and is encapsulated in the hollow portion of the liquid storage portion 401. The support portion 403 is provided at center points of circular side faces of the liquid storage portion 401 and is fixed at a tip end of the shaft 404. The liquid 402 is encapsulated in the liquid storage portion 401 about a half of a capacity of the liquid storage portion 401 and the support portion 403 is provided at a center axis of the liquid storage portion 401. Thus, the liquid 402 has the liquid level 402A that always intersects with the support portion 403.

Figure 19:
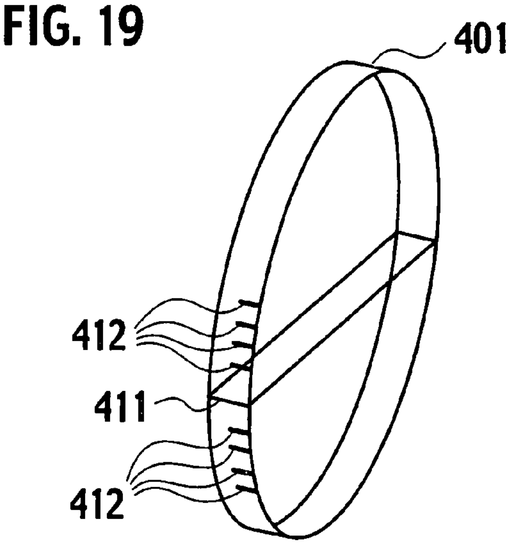
FIG. 19 is a perspective view of a liquid storage portion in the first embodiment of the present invention.

As shown in FIG. 19, the first inclination indicator 411 passes the center point of the circular side faces of the liquid storage portion 401 and goes around the circular side faces and an annular side face of the liquid storage portion 401. On the annular side face of the liquid storage portion 401, the plurality of second inclination indicators 412 are provided at upper and lower sides of the first inclination indicator 411. This allows the liquid storage portion 401 to display the attachment angle of the lower liquid crystal display 301 based on a relative positional relation between the liquid level 402A of the liquid 402 and the first inclination indicator 411 and/or a relative positional relation between the liquid level 402A of the liquid 402 and the second inclination indicators 412. The first inclination indicator 411 and the second inclination indicators 412 are visually and easily recognized from a front face of the lower liquid crystal display 301.

Figure 20:
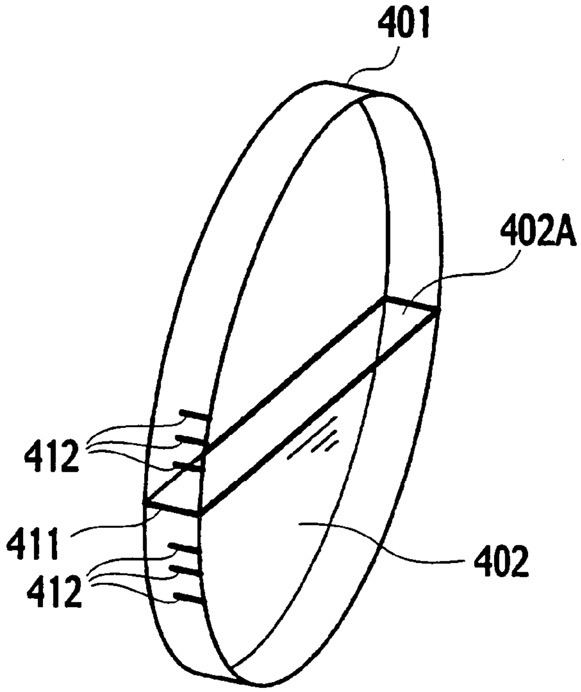
FIG. 20 is a perspective view of the liquid storage portion when the attachment angle of the lower liquid crystal display is the default angle in the first embodiment of the present invention.
Figure 21:
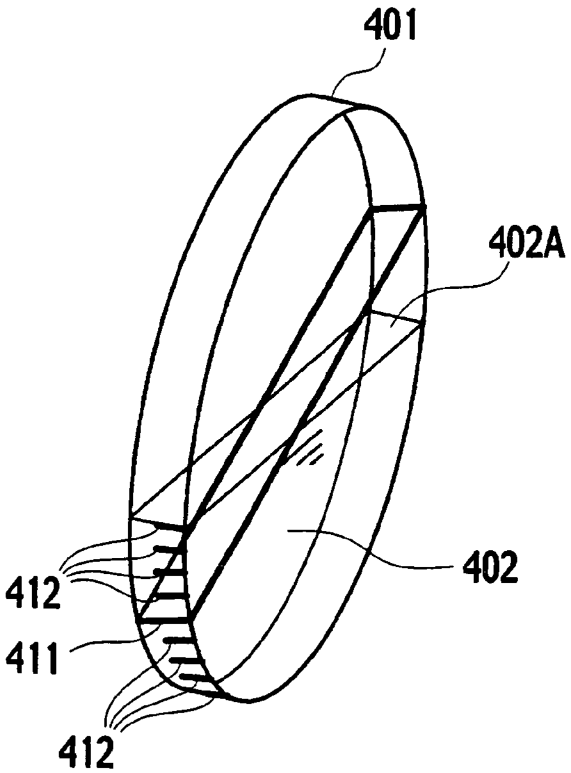
FIG. 21 is a perspective view of the liquid storage portion when the attachment angle of the lower liquid crystal display is the first limit angle in the first embodiment of the present invention.
Figure 22:
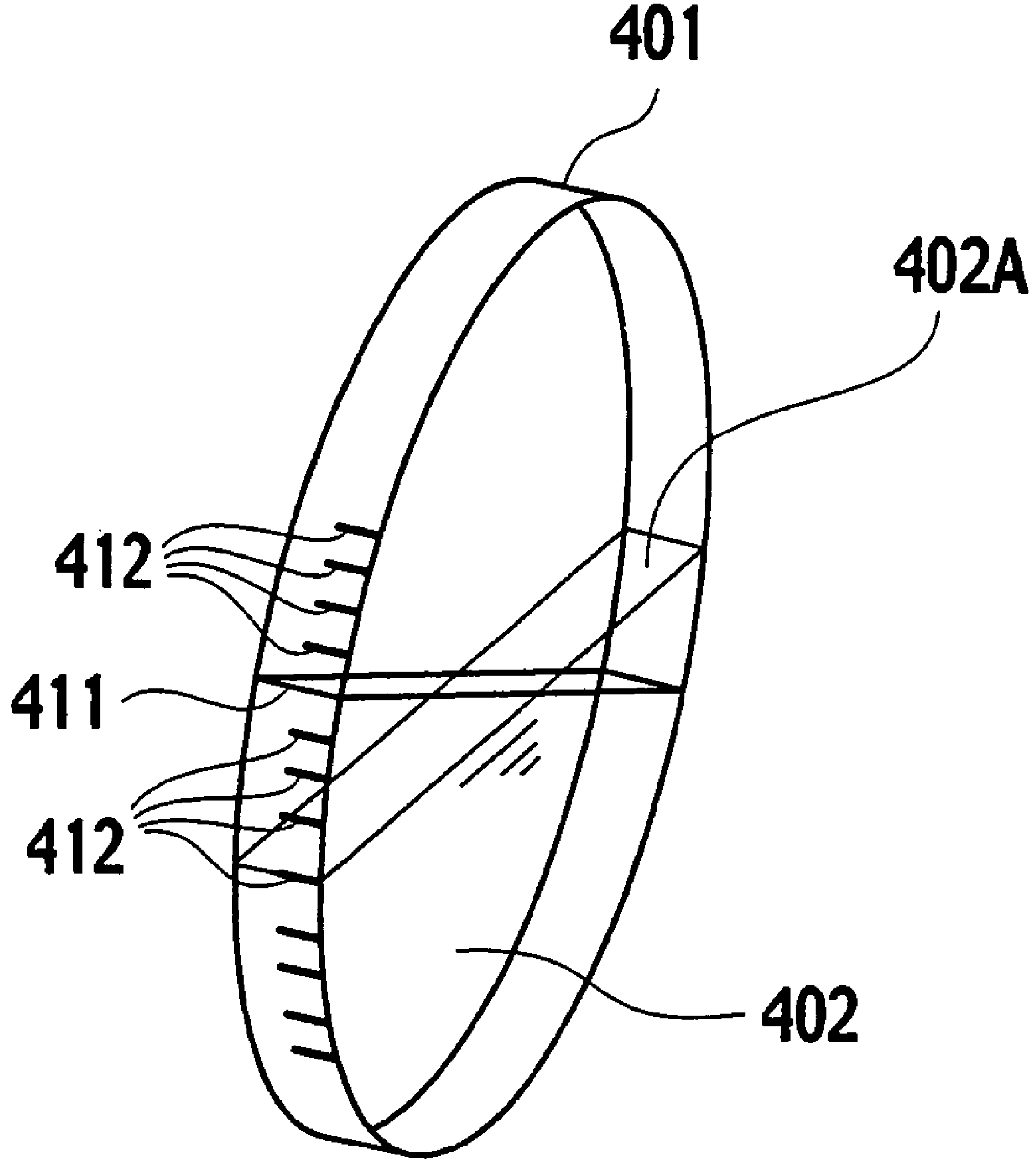
FIG. 22 is a perspective view of the liquid storage portion when the attachment angle of the lower liquid crystal display is the second limit angle in the first embodiment of the present invention.

It is noted that a diameter and a thickness of the liquid storage portion 401 shown in FIG. 1 may be changed if the attachment angle of the lower liquid crystal display 301 can be easily checked from the front face side of the lower liquid crystal display 301. When the attachment angle of the lower liquid crystal display 301 is the default angle $\alpha$0, the liquid level 402A of the liquid 402 completely overlaps with the first inclination indicator 411 as shown in FIG. 20.

Next, an operation of the manual adjustment mechanism 311 will be described.

When a player pushes or pulls the grip 302, the upper parts of the first rollers 331, 331 and the second rollers 332, 332 enter simultaneously in the adjacent concave portions of the wave-like portion 322 against the compression force of the biasing spring 372. Thus, whenever the upper parts of the first rollers 331, 331 and the second rollers 332, 332 enter in the concave portions of the wave-like portion 322, the attachment angle of the lower liquid crystal display 301 is changed.

Figure 5:
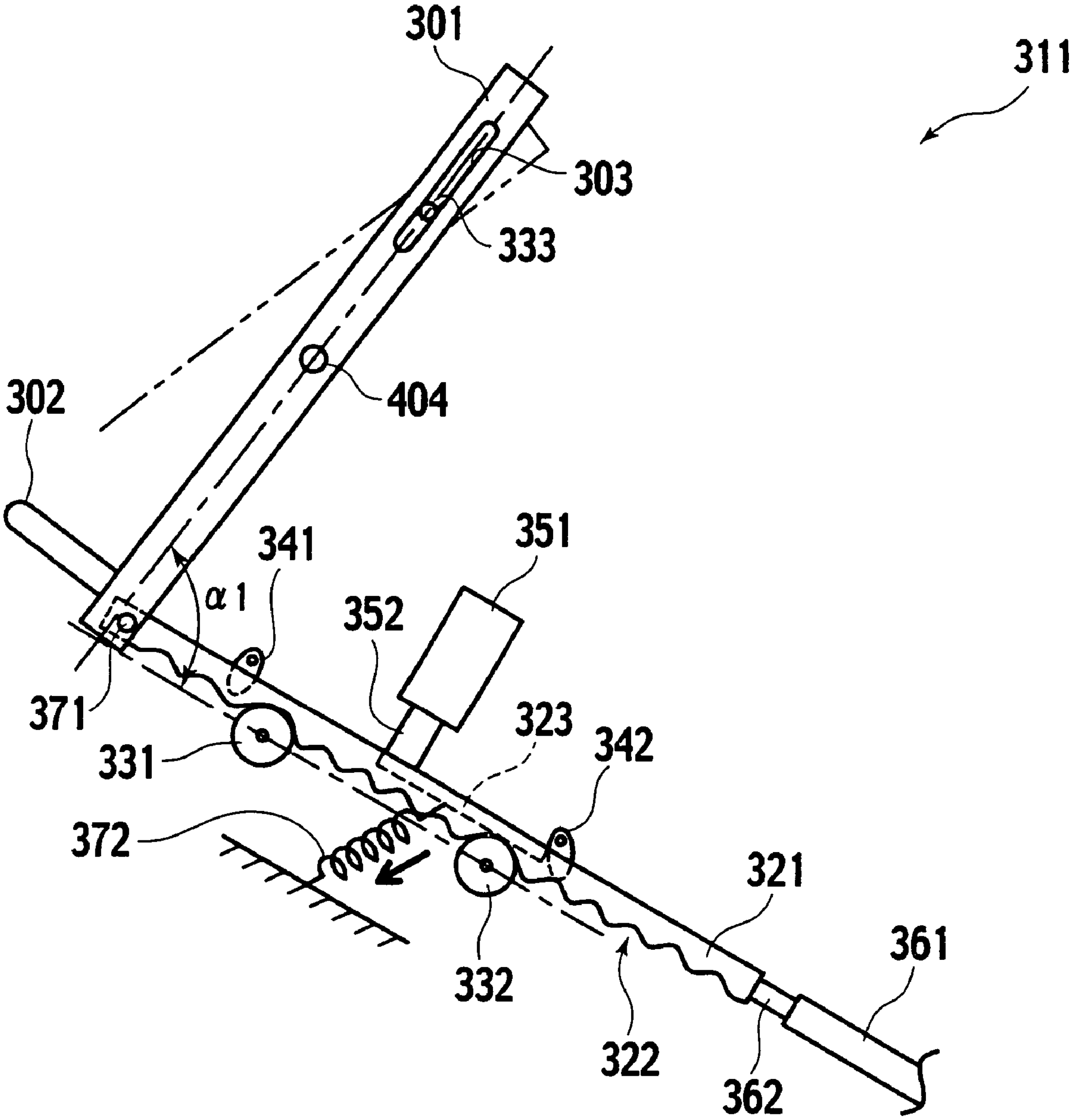
FIG. 5 is a schematic side view of the manual adjustment mechanism when the attachment angle of the lower liquid crystal display is a first limit angle in the first embodiment of the present invention.

When the player continues to push the grip 302, the attachment angle of the lower liquid crystal display 301 reaches a first limit angle $\alpha$1 (see FIG. 5). When the attachment angle reaches the first limit angle $\alpha$1, the lock plate 323 contacts with the second limit switch 342 and then the second limit switch 342 transmits the detection signal to the CPU 50. When the CPU 50 receives the detection signal, the CPU 50 operates the locking actuator 351 so that the rod 351 of the locking actuator 351 pushes the lock plate 323 toward the biasing spring 371. Thus, the upper parts of the first rollers 331, 331 and the second rollers 332, 332 are maintained to be engaged in the concave portions of the wave-like portions 322 of the support base 321. This allows the attachment angle of the lower liquid crystal display 301 (the first limit angle a1) which is rotatably supported by the support base 321 to be retained.

When the player continues to push the grip 302, the attachment angle of the lower liquid crystal display 301 is increased until the attachment angle reaches the first limit angle $\alpha$1. In other words, this operation raises the lower liquid crystal display 301. When the attachment angle is the first limit angle $\alpha$1, the liquid level 402A of the liquid 402 indicates one of the second inclination indicators 412 (see FIG. 21).

Figure 6:
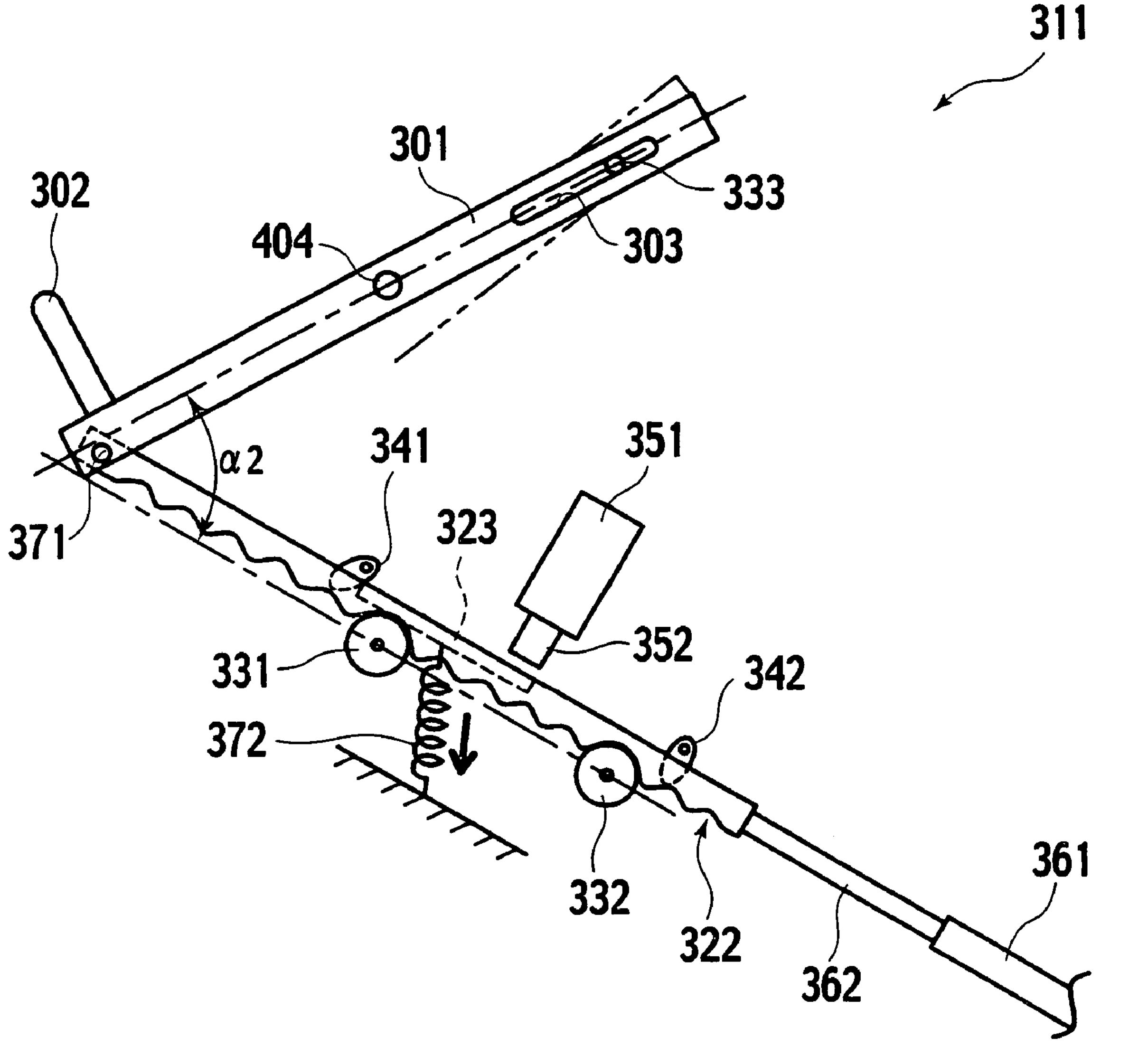
FIG. 6 is a schematic side view of the manual adjustment mechanism when the attachment angle of the lower liquid crystal display is a second limit angle in the first embodiment of the present invention.

On the other hand, when the player continues to pull the grip 302, the attachment angle of the lower liquid crystal display 301 reaches the second limit angle $\alpha$2 (see FIG. 6). When the attachment angle reaches the second limit angle $\alpha$2, the lock plate 323 contacts with the first limit switch 341 and the first limit switch 341 transmits the detection signal to the CPU 50. When the CPU 50 detects the detection signal, the CPU 50 operates the locking actuator 351 so that the rod 351 of the locking actuator 351 pushes the lock plate 323 toward the biasing spring 371. Thus, the upper parts of the first rollers 331, 331 and the second rollers 332, 332 are maintained to be engaged in the concave portions of the wave-like portions 322 of the support base 321. This allows the attachment angle of the lower liquid crystal display 301 (the second limit angle a2) which is rotatably supported by the support base 321 to be retained.

When the player continues to pull the grip 302, the attachment angle of the lower liquid crystal display 301 is reduced until the attachment angle reaches the second limit angle $\alpha$2. In other words, this operation slants the lower liquid crystal display 301. When the attachment angle is the second limit angle $\alpha$2, the liquid level 402A of the liquid 402 indicates one of the second inclination indicators 412 (see FIG. 22).

The first limit switch 341 and the second limit switch 342 function as a means for detecting the position of the lower liquid crystal display 301 because the first limit switch 341 and the second limit switch 342 detects that the attachment angle of the lower liquid crystal display 301 is the second limit angle $\alpha$2 and the first limit angle $\alpha$1. The first limit switch 341 and the second limit switch 342 may be an apparatus for directly detecting the position of the lower liquid crystal display 301 (e.g., infrared radiation sensor) or an apparatus for indirectly detecting the position of the lower liquid crystal display 301 (e.g., encoder).

A manager or a player in a gaming hall can easily check that the attachment angle of the lower liquid crystal display 301 is the first limit angle $\alpha$1 or the second limit angle $\alpha$2 by the relative positional relation between the liquid level 402A of the liquid 402 and the second inclination indicators 412. Also, the manager or the player can easily check that the attachment angle of the lower liquid crystal display 301 is an angle within a range from the first limit angle $\alpha$1 to the second limit angle $\alpha$2 by the relative positional relation between the liquid level 402A of the liquid 402 and the first inclination indicator 411 and/or the relative positional relation between the liquid level 402A of the liquid 402 and the second inclination indicators 412.

It is noted that the moving range of the shaft 404 is designed to be smaller than a diameter of the penetration hole 2A of the cabinet 2, in view of the fact that the shaft 404 provided at the lower liquid crystal display 301 in a protruded manner moves as the attachment angle of the lower liquid crystal display 301 moves from the first limit angle $\alpha$1 to the second limit angle $\alpha$2. Also, the liquid storage portion 401 and the support portion 403 are designed so as not to contact with the penetration hole 2A even when the shaft 404 moves within the above moving range.

Next, the configuration of a control system of the slot machine 1 will be described.

As shown in FIG. 8, the control system of the slot machine 1 comprises the upper liquid crystal display 3, the COLLECT switch 45, the GAME RULES switch 46, the WIN/START switch 47, the GAMBLE RESERVE switch 48, the coin detection sensor 49, the CPU 50, a ROM 51, a RAM 52, a clock pulse generation circuit 53, a frequency dividing circuit 54, a random number generating circuit 55, a random number sampling circuit 56, the 1-BET switch 57, the 2-BET switch 58, the 3-BET switch 59, the 5-BET switch 60, the 8-BET switch 61, the 1-LINE switch 62, the 2-LINES switch 63, the 5-LINES switch 64, the 20-LINES switch 65, the 25-LINES switch 66, the bill sensor 67, a hopper driving circuit 70, a hopper 71, a payout completion signal circuit 72, the coin detecting portion 73, a liquid crystal driving circuit 74, an audio output circuit 79, a speaker 80, the lower liquid crystal display 301, the first limit switch 341, the second limit switch 342, the locking actuator 351 and an actuator output circuit 381.

The CPU 50 is connected to the ROM 51 and the RAM 52. The ROM 51 stores therein a main processing program, a general mode processing program, a bonus mode processing program, a first sortition table for the sortition of a general mode stop-display symbol, a second sortition table for the sortition of a bonus mode stop-display symbol, other various programs and data required for the control of the slot machine 1, and the like. The RAM 52 is a memory for temporarily storing various data executed by the CPU 50.

The CPU 50 is connected to the clock pulse generation circuit 53 for generating a reference clock pulse, the frequency dividing circuit 54, the clock pulse generation circuit 55 for generating random numbers and the random number sampling circuit 56. The random numbers sampled via the random number sampling circuit 56 is used for various sortitions of winning roles or the like.

The CPU 50 is connected to the COLLECT switch 45 attached to the COLLECT button 31, the GAME RULES switch 46 attached to the GAME RULES button 32, the 1-BET switch 57 attached to the BET1 PERLINE button 33, the 2-BET switch 58 attached to the BET2 PERLINE button 34, the 3-BET switch 59 attached to the BET3 PER LINE button 35, the 5-BET switch 60 attached to the BET5 PER LINE button 36, the 8-BET switch 61 attached to the BET8 PER LINE button 37, the WIN/START switch 47 attached to the WIN START FEATURE button 38, the 1-LINE switch 62 attached to the RED PLAY1 LINE button 39, the 2-LINES switch 63 attached to the PLAY2 LINES button 40, the 5-LINES switch 64 attached to the PLAY5 LINES button 41, the 20-LINES switch 65 attached to the PLAY20 LINES button 42, the 25-LINES switch 66 attached to the BLACK PLAY25 LINES button 43 and the GAMBLE RESERVE switch 48 attached to the GAMBLE RESERVE button 44. When each button is depressed, the CPU 50 executes an operation corresponding to the depressed button based on a switch signal outputted from each switch.

The CPU 50 is connected to the coin detection sensor 49 provided at the coin insertion slot 9 and the bill sensor 67 provided at the bill insertion slot 10. The coin detection sensor 49 detects coins inserted via the coin insertion slot 9. The CPU 50 computes the number of the inserted coins based on the coin detection signal outputted from the coin detection sensor 49. The bill sensor 67 detects the type and amount of bills inserted via the bill insertion slot 10. The CPU 50 computes the number of credits equivalent to the amount of the bill based on the bill detection signal outputted from the bill sensor 67.

The CPU 50 is connected to the hopper 71 via the hopper driving circuit 70. When the CPU 50 outputs a driving signal to the hopper driving circuit 70, the hopper 71 pays out a predetermined number of coins via the coin payout slot 15. The CPU 50 is also connected to the coin detecting portion 73 via the payout completion signal circuit 72. The coin detecting portion 73 is provided in the coin payout slot 15. When the coin detecting portion 73 detects that the coin payout slot 15 paid out the predetermined number of coins, the coin detecting portion 73 outputs a coin payout detection signal to the payout completion signal circuit 72. Upon receiving the coin payout detection signal, the payout completion signal circuit 72 outputs a payout completion signal to the CPU 50.

Figure 9:
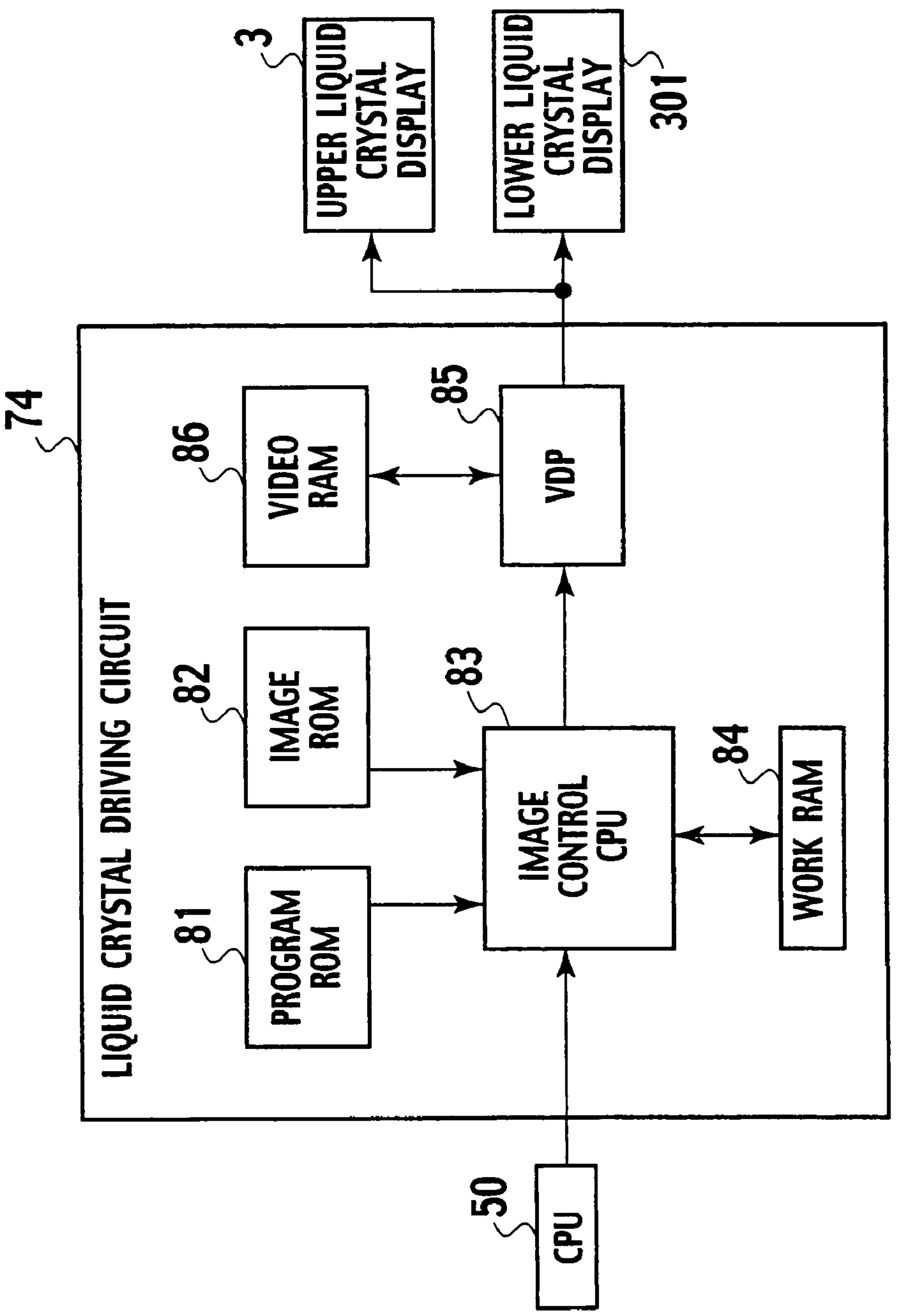
FIG. 9 is a block diagram of a liquid crystal driving circuit of the liquid crystal display in the first embodiment of the present invention.

The CPU 50 is connected to the upper liquid crystal display 3 and the lower liquid crystal display 301 via the liquid crystal driving circuit 74. The CPU 50 controls the upper liquid crystal display 3 and the lower liquid crystal display 301. As shown in FIG. 9, the liquid crystal driving circuit 74 comprises a program ROM 81, an image ROM 82, an image control CPU 83, a work RAM 84, a VDP (video display processor) 85 and a video RAM 86. The program ROM 81 stores therein an image control program and various selection tables regarding the display by the upper liquid crystal display 3 and the lower liquid crystal display 301. The image ROM 82 stores therein, for example, the symbol columns of the reel bands 101, 102, 103, 104, 105 displayed by the lower liquid crystal display 301 (or the variable display portions 21, 22, 23, 24, 25) and dot data for forming an image to be demonstrated. The image control CPU 83 determines an image to be displayed by the upper liquid crystal display 3 or the lower liquid crystal display 301 among the dot data previously stored in the image ROM 82 based on parameters set by the CPU 50 and an image control program previously stored in the program ROM 81. The work RAM 84 is a temporary storage means. The work RAM 84 allows the image control CPU 83 to execute an image control program. The VDP 85 forms an image in accordance with display contents determined by the image control CPU 83 to output the image to the upper liquid crystal display 3 or the lower liquid crystal display 301. This allows the lower liquid crystal display 301 to display the symbol columns of the reel bands 101, 102, 103, 104, 105 in the variable display portions 21, 22, 23, 24, 25 in a scrolling manner, for example. The video RAM 86 is a temporary storage means. The video RAM 86 allows the VDP 85 to form the image.

The CPU 50 is connected to the audio output circuit 79 and the speaker 80. The speaker 80 generates sound effects when various effects are performed based on an output signal from the audio output circuit 79. The CPU 50 is connected to the locking actuator 351 via the first limit switch 341, the second limit switch 342 and the actuator output circuit 381.

Here, the first sortition table will be described. The first sortition table is used to determine symbols stop-displayed on a validated payline which is composed of the second stop-display regions 212, 222, 232, 242, 252 of the variable display portions 21, 22, 23, 24, 25 when the slot machine 1 performs the general mode in the variable display portions 21, 22, 23, 24, 25.

In order to determine the symbols stop-displayed on the validated payline every the second stop-display regions 212, 222, 232, 242, 252, thirty symbols which composes the symbol columns of the respective reel bands are allocated with code numbers of “00” to “29” in this order from the top (see FIG. 10). On the other hand, the first sortition table previously allocates one random number value to each code number. Then, five random number values corresponding to the second stop-display regions 212, 222, 232, 242, 252 are sampled by the random number sampling circuit 56, thereby determining the symbols stop-displayed on the validated payline.

Next, winning combinations and dividends to the winning combinations will be described in a case where the slot machine 1 uses the variable display portions 21, 22, 23, 24, 25 to perform the general mode. FIG. 11 shows dividends when the bet number is “1”. When the bet number is “1”, the value of the dividend shown in FIG. 11 is added to the credit. When the bet number is “2” or more, a value obtained by multiplying the value of the dividend shown in FIG. 11 by an associated bet number is added to the credit.

More specifically, when two symbols of “WILD” are continuously stop-displayed on the validated payline on the variable display portions 21, 22 (in the case of “2K” which means two symbols appear continuously from the left end), the dividend of “10” is obtained. When three symbols of “WILD” are continuously stop-displayed on the validated payline on the variable display portions 21, 22, 23 (in the case of “3K” which means three patterns appear continuously from the left end), the dividend of “320” is obtained. When four symbols of “WILD” are continuously stop-displayed on the validated payline on the variable display portions 21, 22, 23, 24 (in the case of “4K” which means four symbols appear continuously from the left end), the dividend of “2500” is obtained. When five symbols of “WILD” are continuously stop-displayed on the validated payline on the variable display portions 21, 22, 23, 24, 25 (in the case of “5K” which means five symbols appear from the left end), the dividend of “6000” is obtained.

When two symbols of “SHARK” are continuously stop-displayed on the validated payline on the variable display portions 21, 22 (in the case of “2K”), the dividend of “3” is obtained. When three symbols of “SHARK” are continuously stop-displayed on the validated payline on the variable display portions 21, 22, 23 (in the case of “3K”), the dividend of “25” is obtained. When four symbols of “SHARK” are continuously stop-displayed on the validated payline on the variable display portions 21, 22, 23, 24 (in the case of "4K"), the dividend of "150" is obtained. When five symbols of "SHARK" are continuously stop-displayed on the validated payline on the variable display portions 21, 22, 23, 24, 25 (in the case of "5K"), the dividend of "1000" is obtained. It is noted that the symbol of "SHARK" can be substituted by the symbol of "WILD".

In the same manner as described above, the dividends as shown in FIG. 11 are obtained for each of the symbols of "FISH", "PUNK", "OCTOPUS", "CRAB", "WORM", "A", "K", "Q" and "J". It is noted that the above symbols can be substituted by the symbol of "WILD". When these symbols appear on a plurality of validated paylines, the total of dividends of these symbols is added to the credit.

Finally, when two symbols of "SARDIN" appear (are stop-displayed) on the variable display portions 21, 22, 23, 24, 25 independent of the validated payline, in other words in the case of "2K", the dividend of "2" is obtained. When three symbols of "SARDIN" appear (are stop-displayed), in other words in the case of "3K", the dividend of "5" is obtained. When four symbols of "SARDIN" appear (are stop-displayed), in other words in the case of "4K", the dividend of "10" is obtained. When five symbols of "SARDIN" appear (are stop-displayed), in other words in the case of "5K", the dividend of "125" is obtained.

Regarding dividends by the symbol of "SARDIN", a value obtained by multiplying the value of the dividend shown in FIG. 11 with a total bet number (which is a product of the bet number with the number of validated paylines) is added to the credit. If there is a dividend by a symbol other than "SARDIN", the dividend is also added to the credit.

When three or more symbols of "SARDIN" appear (are stop-displayed) on the variable display portions 21, 22, 23, 24, 25 independent of the validated payline, the above dividend is obtained and the current mode is switched to the bonus mode. When the current mode is switched to the bonus mode, symbol columns displayed variably on the variable display portions 21, 22, 23, 24, 25 are the symbols of the reel bands 101, 102, 103, 104, 105 shown in FIG. 10, which are the same as the symbol columns used in the general mode.

The bet number and the number of validated paylines in the bonus mode are the bet number and the number of validate paylines determined at the time of switching the current mode to the bonus mode. Winning combinations and dividends to the winning combinations in the bonus mode are the same as the winning combinations and the dividends to the winning combinations in the general mode except that the symbol of "SHARK" is regarded as the symbol of "WILD" and the mode is switched to the bonus mode again when three symbols of "SARDIN" appear (are stop-displayed).

Next, the main processing program of the slot machine 1 will be described.

Figure 13:
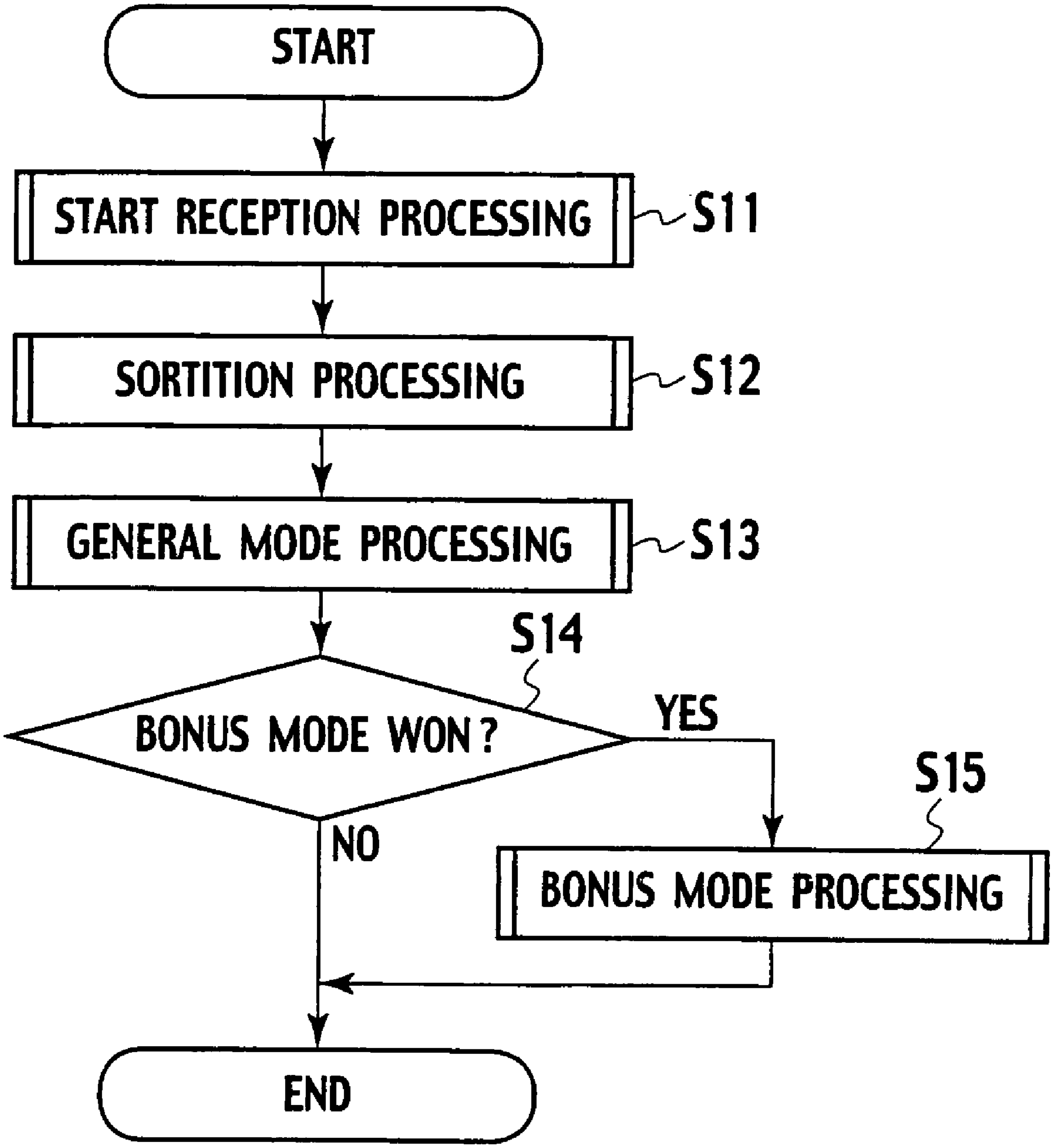
FIG. 13 is a flowchart of a main processing program in the first embodiment of the present invention.
Figure 14:
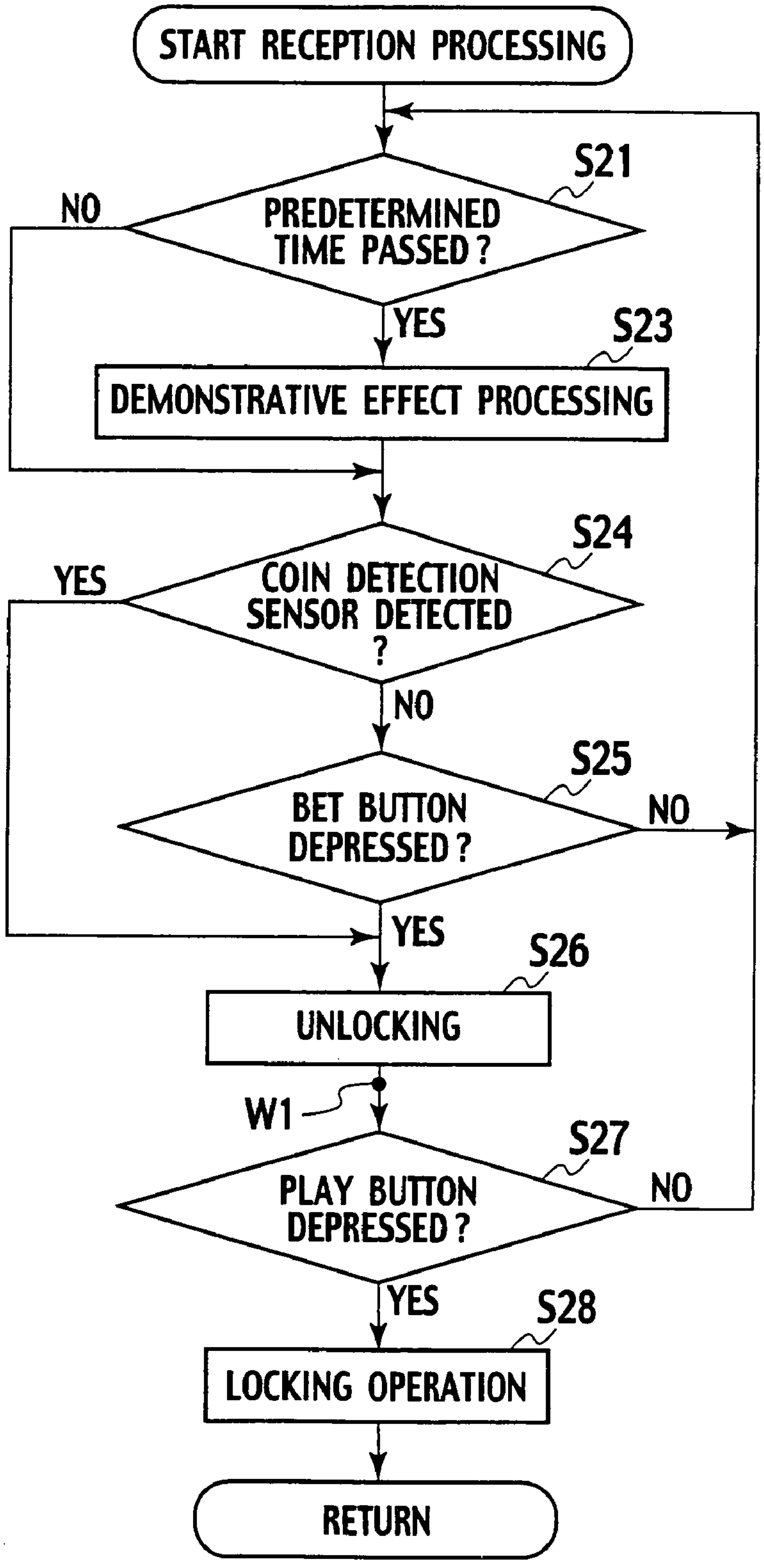
FIG. 14 is a flowchart of a start reception processing program in the first embodiment of the present invention.

As shown in FIG. 13, Step S11 allows the CPU 50 to perform the start reception processing (see FIG. 14). In the start reception processing, the CPU 50 receives the coin detection signal outputted from the coin detection sensor 49 or receives the switch signals outputted from the 1-BET switch 57, the 2-BET switch 58, the 3-BET switch 59, the 5-BET switch 60, or the 8-BET switch 61 and the 1-LINE switch 62, the 2-LINES switch 63, the 5-UNES switch 64, the 20-UNES switch 65 or the 25-LINES switch 66 based on the operation of the BET1 PER LINE button 33, the operation of the BET2 PER LINE button 34, the operation of the BET3 PER LINE button 35, the operation of the BET5 PER LINE button 36 or the operation of the BET8 PER LINE button 37, and the operation of the RED PLAY1 LINE button 39, the operation of the PLAY2 LINES button 40, the operation of the PLAY5L LINES button 41, the operation of the PLAY20 LINES button 42 or the operation of the BLACK PLAY25 LINES button 43. When the CPU 50 receives the switch signals, the slot game is started.

Figure 15:
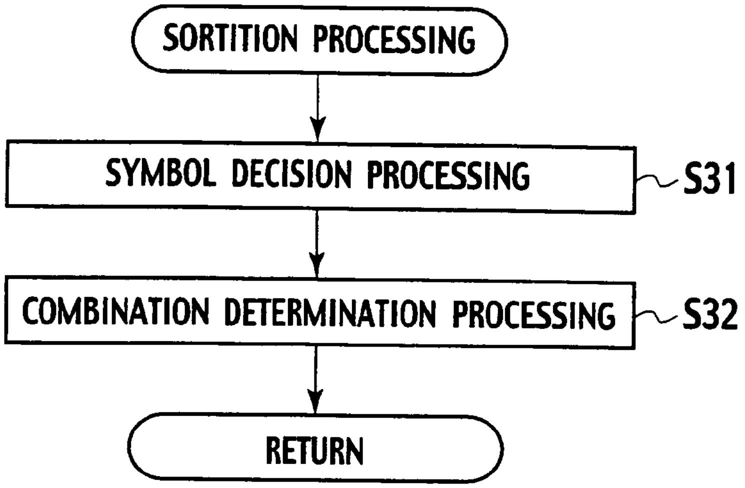
FIG. 15 is a flowchart of a sortition processing program in the first embodiment of the present invention.

Step S12 allows the CPU 50 to perform the sortition processing based on the switch signal outputted from the 1-LINE switch 62, the 2-LINES switch 63, the 5-LINES switch 64, the 20-LINES switch 65 or the 25-LINES switch 65 (see FIG. 15). When the bonus mode is won in the sortition processing, the number of repetition of the bonus modes is determined (e.g., one number is selected from among 10 to 25 by lottery).

Figure 16:
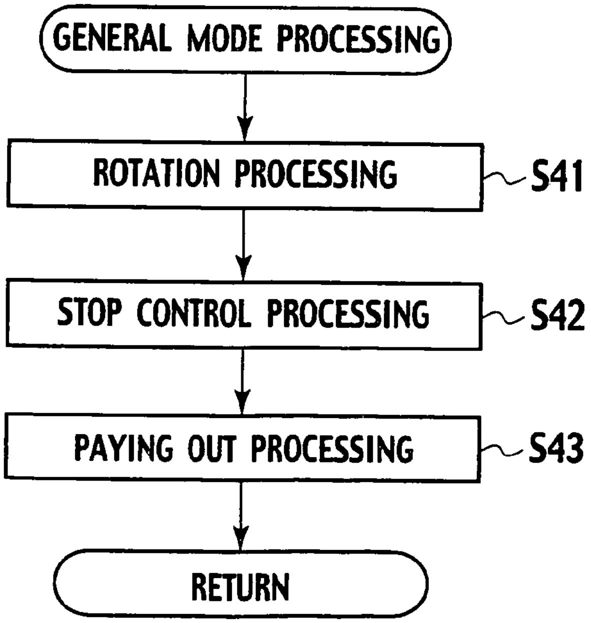
FIG. 16 is a flowchart of a general mode processing program in the first embodiment of the present invention.

Step S13 allows the CPU 50 to perform the general mode processing (see FIG. 16). Step S14 allows the CPU 50 to determine whether the bonus mode is won or not. More specifically, in Step S12, when three or more symbols of "SARDIN" appear (are stop-displayed) in the variable display portions 21, 22, 23, 24, 25 independent of the validated payline(s), the bonus mode is won (Step S14: YES). Thus, the CPU 50 proceeds to Step S15 to perform the bonus game mode processing and then subsequently complete the main processing program. On the other hand, when three or more symbols of "SARDIN" do not appear (are stop-displayed) in the variable display portions 21, 22, 23, 24, 25 independent of the validated payline(s), the bonus mode is not won (Step S14: NO). Thus, the CPU 50 completes the main processing program.

Next, the start reception processing program performed in Step S11 of the main processing program will be described in detail.

As shown in FIG. 14, Step S21 allows the CPU 50 to determine whether a predetermined time (e.g., 15 seconds) has passed or not. When the predetermined time has not passed (Step S21: NO), the CPU 50 proceeds to Step S24. When the predetermined time has passed (Step S21: YES), the CPU 50 proceeds to Step S23 to display a demonstration image on the upper liquid crystal display 3 or the lower liquid crystal display 301.

Step S24 allows the CPU 50 to determine whether the coin detection sensor 49 detects a coin or not. This determination is performed based on whether the CPU 50 receives the coin detection signal from the coin detection sensor 49 or not. When the coin detection sensor 49 detects the coin (Step S24: YES), the CPU 50 proceeds to Step S26. When the coin detection sensor 49 does not detect the coin (Step S24: NO), the CPU 50 proceeds to Step S25.

Step S25 allows the CPU 50 to determine whether the operation of the BET1 PERLINE button 33, the operation of the BET2 PERLINE button 34, the operation of the BET3 PER LINE button 35, the operation of the BET5 PER LINE button 36 or the operation of the BET8 PER LINE button 37 is performed or not. When the button operation is not performed (Step S25: NO), the CPU 50 returns to Step S21. When the button operation is performed (Step S25: YES), the CPU 50 proceeds to Step S26.

Step S26 allows the CPU 50 to perform unlocking. More specifically, the CPU 50 allows the rod 352 of the locking actuator 351 to release pushing the lock plate 323. When a player pushes or pulls the grip 302 while the unlocking status is maintained, a plurality of convex portions of the wave-like portions 323 provided at the bottom face of the support base 321 go over the first rollers 331, 331 and the second rollers 332, 332 simultaneously. Thus, whenever the convex portions go over the rollers, the attachment angle of the lower liquid crystal display 301 is changed.

Step S27 allows the CPU 50 to determine whether the operation of the RED PLAY1 LINE button 39, the operation of the PLAY2 LINES button 40, the operation of the PLAY5

LINES button 41, the operation of the PLAY20 LINES button 42 or the operation of the BLACK PLAY25 LINES button 43 is performed or not. When the button operation is not performed (Step S27: NO), the CPU 50 returns to Step S21. When the operation of the button 39 is performed (Step S27: YES), the CPU 50 proceeds to Step S28. It is noted that the CPU 50 in Step S27 may also perform the above determination based on other input signals, regardless the button operation.

Step S28 allows the CPU 50 to perform a locking operation. More specifically, the CPU 50 allows the rod 352 of the locking actuator 351 to press the lock plate 323, thereby fixing the attachment angle of the lower liquid crystal display 301. Then, the CPU 50 returns to the main processing program and then performs the sortition processing.

Figure 18:
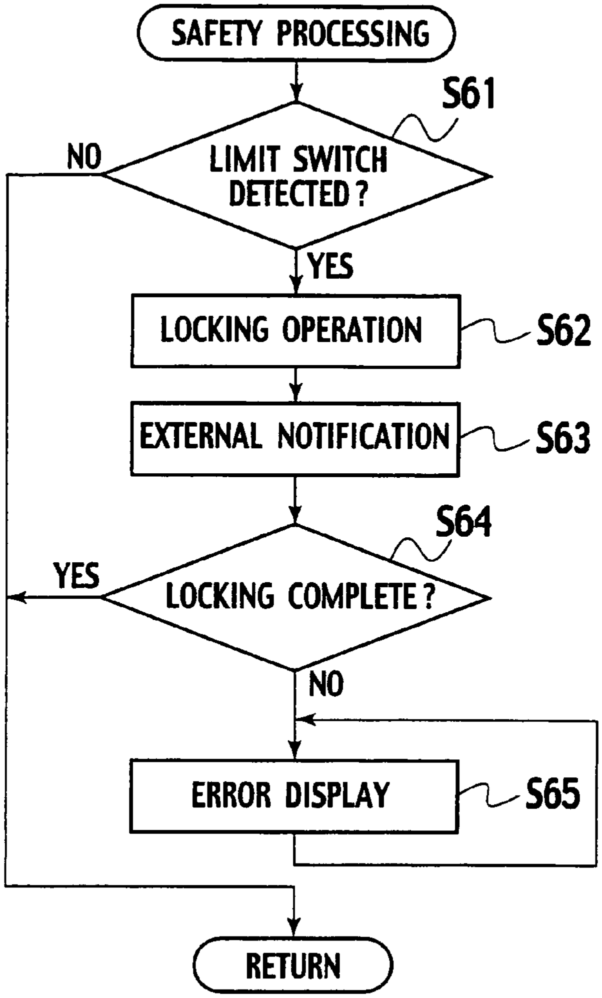
FIG. 18 is a flowchart of a safety processing program in the first embodiment of the present invention.

Here, it is noted that a time point W1 between Step S26 and Step S27 allows the CPU 50 to perform a safety processing (see FIG. 18). Step S61 allows the CPU 50 to determine whether detection by the limit switch is performed or not. More specifically, the CPU 50 determines whether the detection signal which is transmitted when the first limit switch 341 or the second limit switch 342 detects the lock plate 323 is received or not. When the limit switch does not detect the lock plate 323 (Step S61: NO), the CPU 50 proceeds to Step S27.

When the limit switch detects the lock plate 323 (Step S61: YES), the CPU 50 proceeds to Step S62 to perform a locking operation. More specifically, the rod 352 of the locking actuator 351 presses the lock plate 323 of the support base 323, thereby fixing the attachment angle (e.g., the first limit angle α1, the second limit angle α2) of the lower liquid crystal display 301.

Step S63 allows the CPU 50 to perform an external notification. More specifically, when the attachment angle of the lower liquid crystal display 301 reaches the first limit angle α1 or the second limit angle α2, the CPU 50 displays, on the lower liquid crystal display 301, that the angle exceeds the change range of the attachment angle and emits sound from the speaker 80. Step S64 allows the CPU 50 to determine whether a locking is completed or not. When the locking is completed (Step S64: YES), the CPU 50 proceeds to step S27. When the locking is not completed (Step S64: NO), the CPU 50 proceeds to step S65. Step S65 allows the CPU 50 to display "ERROR" on the upper liquid crystal display 3 and then interrupt the processing, thereby stopping the slot game.

Next, the sortition processing program performed by Step S12 of the main processing program will be described.

As shown in FIG. 15, Step S31 allows the CPU 50 to perform a symbol decision processing. In the symbol decision processing, the CPU 50 decides symbols to be stop-displayed on the first payline in the general mode. More specifically, the CPU 50 causes the random number sampling circuit 56 to sample five random number values respectively corresponding to the second stop-display regions 212, 222, 232, 242, 252 and then decide stop-display symbols via the code numbers respectively equivalent to the sampled random number values, based on the first sortition table.

Step S32 allows the CPU 50 to perform a combination determination processing. In the combination determination processing, the CPU 50 decides winning combinations and dividends to the winning combinations via the code numbers used in Step S31, based on the table of FIG. 11. It is noted that the first payline is composed of the second stop-display regions 212, 222, 232, 242, 252.

Next, the general mode processing program performed in Step S13 of the main processing program will be described.

As shown in FIG. 16, Step S41 allows the CPU 50 to display variably the symbols on the variable display portions 21, 22, 23, 24, 25, based on the switch signal outputted from the 1-LINE switch 62, the 2-LINES switch 63, the 5-LINES switch 64, the 20-LINES switch 65 or the 25-LINES switch 65 that is received in Step S11 of FIG. 13. Step S42 allows the CPU 50 to stop-display the symbols on the variable display portions 21, 22, 23, 24, 25.

Step S43 allows the CPU 50 to pay out credit or the like corresponding to the dividend decided based on the combination of symbols (the winning combination) stop-displayed on the second stop-display regions 212, 222, 232, 242, 252, based on the table of FIG. 11.

Next, the bonus mode processing program performed in Step S15 of the main processing program will be described.

Figure 17:
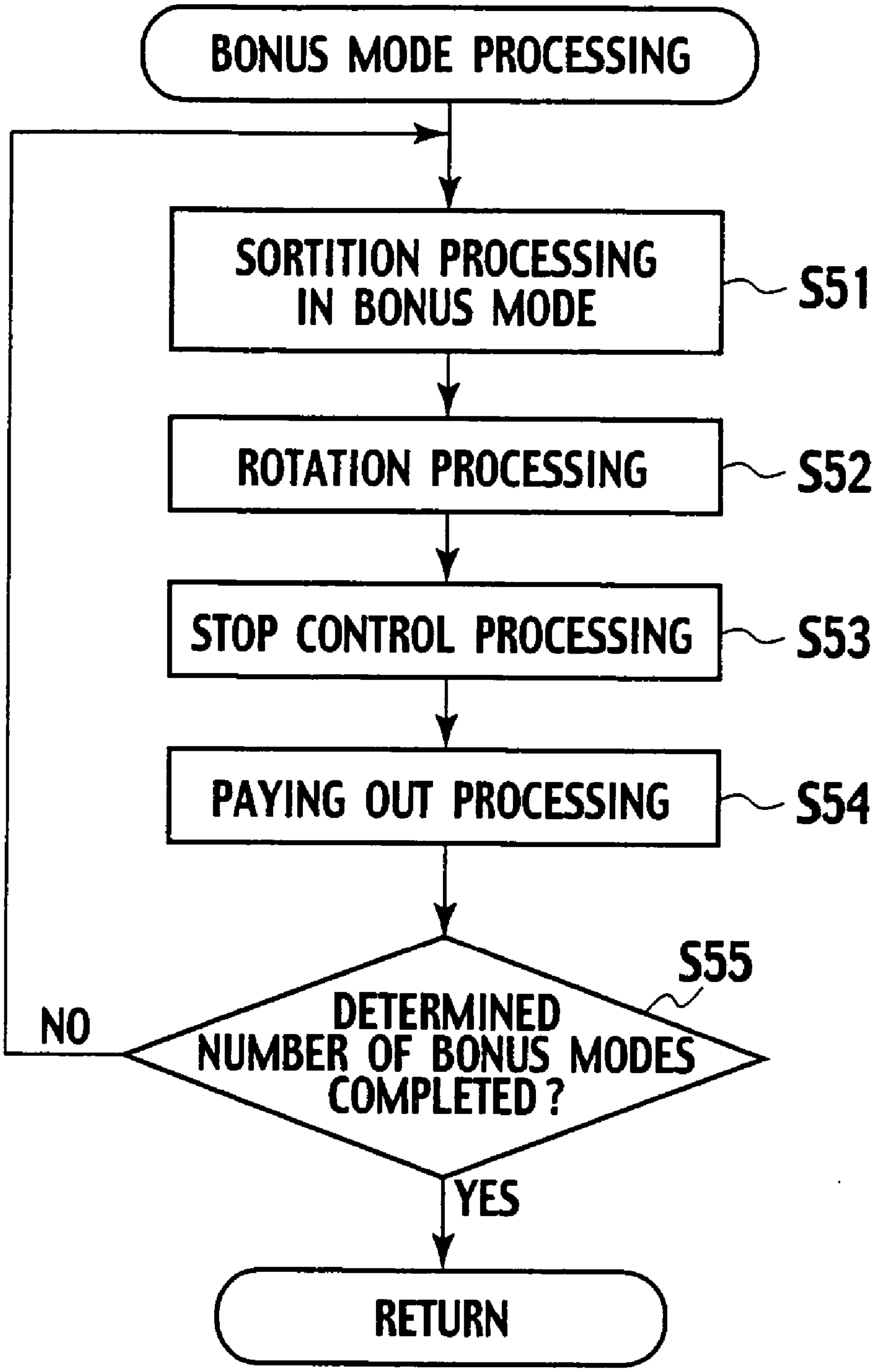
FIG. 17 is a flowchart of a bonus mode processing program in the first embodiment of the present invention.

As shown in FIG. 17, Step S51 allows the CPU 50 to perform the sortition processing in the bonus mode. In the sortition processing, the CPU 50 decides the symbols stop-displayed on the first payline in the bonus game. More specifically, the CPU 50 causes the random number sampling circuit 56 to sample five random number values respectively corresponding to the second stop-display regions 212, 222, 232, 242, 252 and then decide stop-display symbols via the code numbers respectively equivalent to the sampled random number values, based on the second sortition table. When the CPU 50 decides the symbols stop-displayed on the first payline, the CPU 50 decides winning combinations and dividends to the winning combinations via these code numbers, based on the table of FIG. 11.

Step S52 allows the CPU 50 to perform a rotation processing. In the rotation processing, the CPU 50 variably displays the symbols on the variable display portions 21, 22, 23, 24, 25. Step S53 allows the CPU 50 to perform a stop control processing. In the stop control processing, the CPU 50 stop-displays symbols on the variable display portions 21, 22, 23, 24, 25.

Step S54 allows the CPU 50 to perform a payout processing. In the payout processing, the CPU 50 pays out credit or the like corresponding to a dividend decided based on the combination of symbols (the winning combination) stop-displayed on the second stop-display regions 212, 222, 232, 242, 252 in Step S53, based on the table of FIG. 11 (however the symbol of "SHARK" is regarded as the symbol of "WILD").

Step S55 allows the CPU 50 to determine whether the number of bonus mode executions reaches the number decided by Step S12 of FIG. 13 or not. When the number of bonus mode executions does not reach the number decided by Step S12 of FIG. 13 (Step S55: NO), the CPU 50 returns to Step S51. When the number of bonus mode executions reaches the number decided by Step S12 of FIG. 13 bonus mode (Step S55: YES), the CPU 50 completes the bonus mode processing program.

When the bonus mode is won in Step S51, the number of repetition of the bonus game is newly decided. The decided repetition number is added to the number decided by Step S12 of FIG. 13 in the determination of Step S55. This allows the bonus mode to be switched to the bonus mode again when a player wins a bonus mode during the bonus mode. More specifically, for example, when a general mode is switched to 20 bonus modes and the 12th bonus mode in the 20 bonus modes newly wins 17 bonus modes, 25 (=20−12+17) bonus modes can be performed. When a player finally obtains a credit in the bonus modes, the double down game for betting the obtained credit may be performed (the description of the double down game is omitted) after the bonus modes are completed.

Next, advantageous characteristics of the slot machine 1 will be described.

When a manager or a player in a gaming hall pushes or pulls the grip 302 provided at the lower liquid crystal display 301, the upper parts of the first rollers 331, 331 and the second rollers 332, 332 go over the convex portions of the wave-like portion 322 formed on the bottom face of the support base 321 and then move to the concave portions adjacent to the convex portions to be retained therein while the support base 321 is compressed toward the first rollers 331,331 and the second rollers 332, 332 by the biasing spring 372. Therefore, whenever the upper parts of the first rollers 331, 331 and the second rollers 332, 332 go over the convex portions of the wave-like portion 322, the lower liquid crystal display 301 is raised or slanted in a stepwise manner. Further, the inclination (attachment angle) of the lower liquid crystal display 301 with respect to the cabinet 2 is maintained.

A manager or a player in the gaming hall can easily check the attachment angle of the lower liquid crystal display 301 via the liquid storage portion 401, from the front face of the slot machine 1 based on the relative positional relation between the liquid level 402A of the liquid 402 and the first inclination indicator 411 and/or the relative positional relation between the liquid level 402A of the liquid 402 and the second inclination indicators 412. Therefore, if the player once memorizes the relative positional relation between the liquid level 402A and the first inclination indicator 411 (and/or the second inclination indicators 412) corresponding to an attachment angle that is most preferable to the player, he/she may easily adjust the lower liquid crystal display 301 so as to reproduce the memorized relative positional relation when adjusting the attachment angle of the lower liquid crystal display 301 next time. Further, if the manager in the gaming hall once memorizes the relative positional relation between the liquid level 402A and the first inclination indicator 411 (and/or the second inclination indicators 412) corresponding to a predetermined angle (e.g., default angle $\alpha\mathbf{0}$) in order to equalize the attachment angles of the lower liquid crystal displays 301 of the plurality of slot machines 1 with which no player plays the slot game, he/she can easily adjust the attachment angles of the lower liquid crystal displays 301 of the plurality of slot machines 1 so as to set the attachment angles to the predetermined angle. This improves the appearance of the gaming hall.

The liquid storage portion 401 is made of a transparent plastic and is filled with the liquid 402 colored by fluorescent paint. Therefore, players can enjoy the colorful appearance of the slot machine 1.

Next, a modification of this embodiment will be described.

Figure 23:
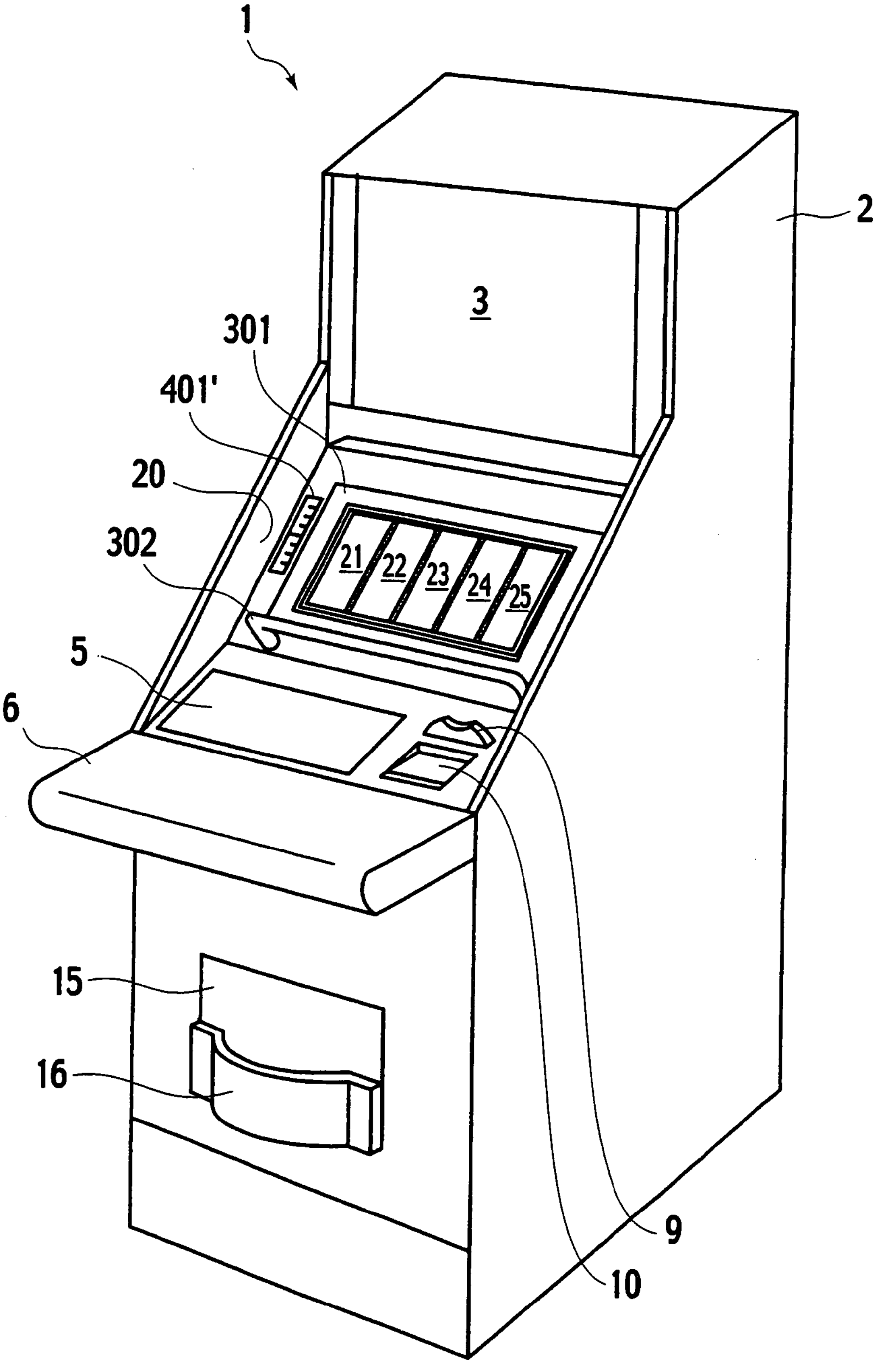
FIG. 23 is a perspective view of a slot machine in a modification of the first embodiment of the present invention.
Figure 24:
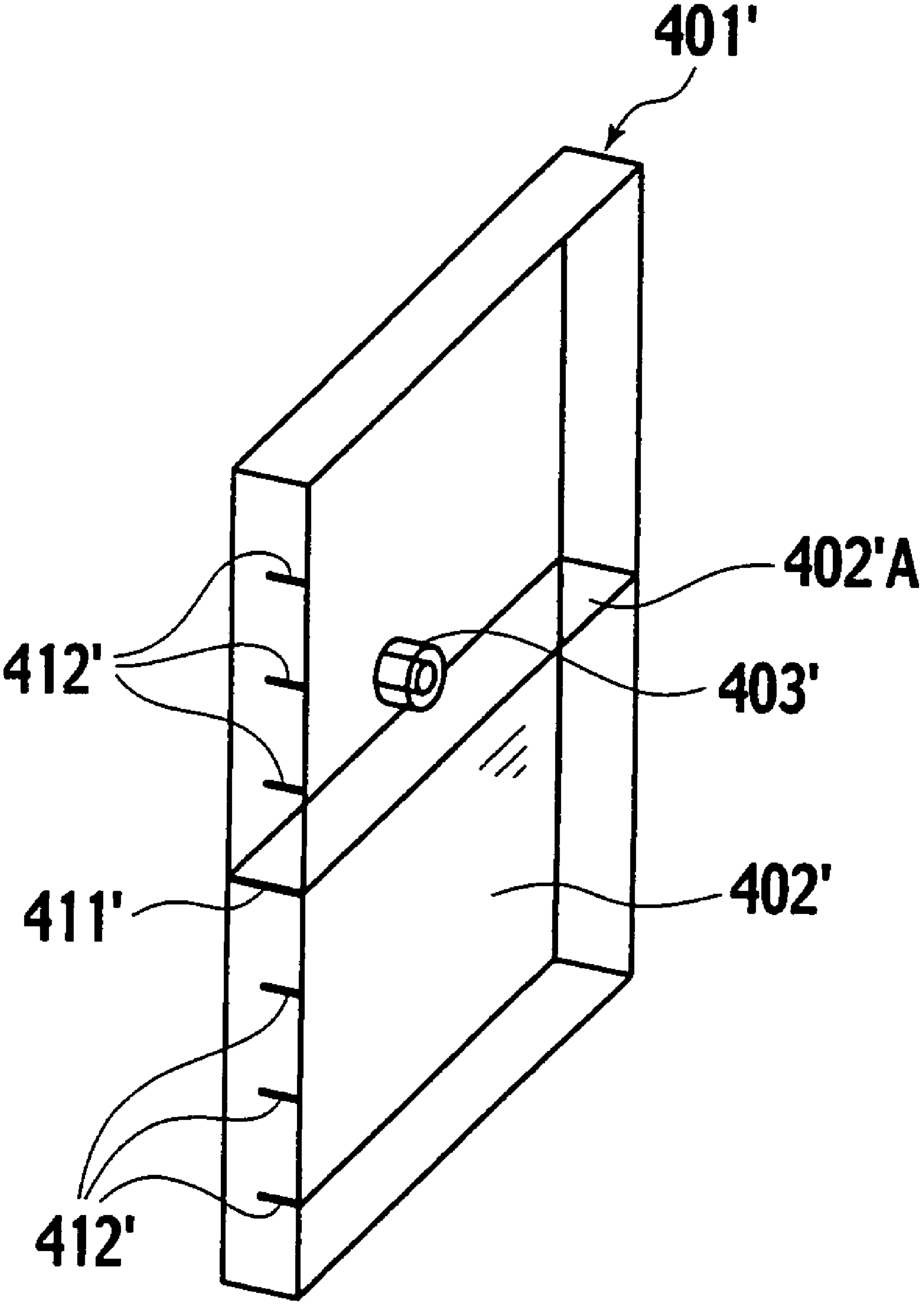
FIG. 24 is a perspective view of a liquid storage portion when the attachment angle of the lower liquid crystal display is the default angle in the modification of the first embodiment of the present invention.

As shown in FIG. 23, the liquid storage portions 401, 401 provided at both side faces of the cabinet 2 may be changed to a liquid storage portion 401' provided at an end part of the lower liquid crystal display 301. As shown in FIG. 24, the liquid storage portion 401' is made of a transparent plastic which has a cuboid-like shape and has a hollow part therein. The liquid storage portion 401' has a front face to be exposed from the lower liquid crystal display 301. The liquid storage portion 401' comprises liquid 402', a support portion 403', a first inclination indicator 411' and a plurality of second inclination indicators 412'. The liquid 402' is colored by fluorescent paint and is encapsulated in the hollow part of the liquid storage portion 401'. The support portion 403' is provided at center points of side faces of the liquid storage portion 401' and is fixed to a tip end of the shaft 404. It is noted that the shaft 404 in this modification is provided at one side face of the lower liquid crystal display 301 in a protruded manner and is stored in the cabinet 2. The liquid 402' is encapsulated in the liquid storage portion 401' about a half of the inner capacity of the liquid storage portion 401' and the support portion 403' is provided at the center points of the liquid storage portion 401'. Thus, the liquid 402 has the liquid level 402A' that always intersects with the support portion 403'.

The first inclination indicator 411' passes the center points of the side faces of the liquid storage portion 401' and goes around the side faces, the front face and a back face of the liquid storage portion 401'. A plurality of second inclination indicators 412' are provided at the upper and lower sides of the first inclination indicator 411' on the front face of the liquid storage portion 401'. When the attachment angle of the lower liquid crystal display 301 is the default angle $\alpha\mathbf{0}$, a liquid level 402A' of the liquid 402' completely overlaps with the first inclination indicator 411'. Thus, the liquid storage portion 401' displays the attachment angle of the lower liquid crystal display 301 based on the relative positional relation between the liquid level 402'A of the liquid 402' and the first inclination indicator 411' and/or the relative positional relation between the liquid level 402'A of the liquid 402' and the second inclination indicators 412'. The first inclination indicator 411' and the second inclination indicator 412' are visually and easily recognized from the front face of the lower liquid crystal display 301.

Next, another modification of this embodiment will be described.

In the slot machine 1 with which no player plays the slot game, the attachment angle of the lower liquid crystal display 301 may be automatically returned to the default angle $\alpha\mathbf{0}$. In a plurality of slot machines 1 with which no player plays the slot game, this provides a uniform attachment angle to the plurality of lower liquid crystal displays 301, thus improving the appearance of the gaming hall. Further, when the default angle $\alpha\mathbf{0}$ is an angle through which a moving player can visually recognize the lower liquid crystal display 301 and when the lower liquid crystal display 301 of the slot machine 1 with which no player plays the slot game displays a demonstration image, the moving player can see the demonstration image. This may attract more customers.

The slant-type cabinet 2 which makes a player sit on a chair to play the slot game may be changed to an upright type cabinet which makes a player to stand to play the slot game.

The number of video reels used in the slot machine 1 is not limited to five and may be three or nine. The video reel used in the slot machine 1 also may be changed to a mechanical reel. Alternatively, the slot machine 1 also may be changed to a hybrid type slot machine that uses both of a video reel and a mechanical reel.

Instead of providing the liquid storage portions 401, 401 to both side faces of the cabinet 2, the liquid storage portion 401 may be provided at one side face of the cabinet 2.

The slot machine 1 also may be changed to a gaming machine that provides another type of game (e.g., card game, shooting game). The liquid storage portion of this embodiment also may be used for a television provided in airplanes or the like in order to display the attachment angle of the television.

Second Embodiment

This embodiment is different from the first embodiment in the configuration of a slot machine and the mechanism for adjusting the attachment angle of the lower liquid crystal display. The same members as those in the first embodiment will be denoted with the same reference numerals and will not be described in detail.

Figure 25:
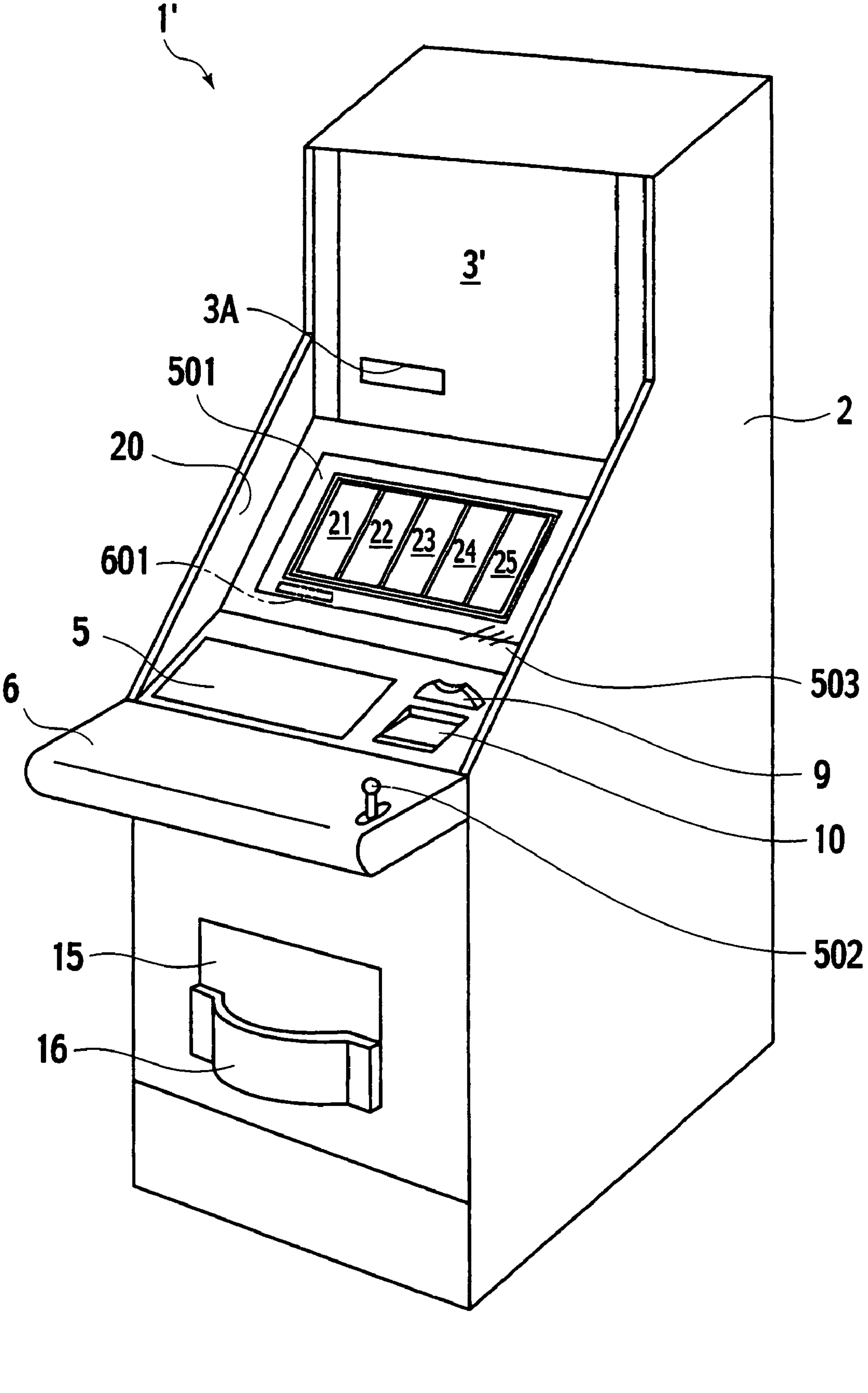
FIG. 25 is a perspective view of a slot machine in a second embodiment of the present invention.

As shown in FIG. 25, a gaming machine (slot machine in this embodiment) 1' comprises the cabinet 2, an upper liquid crystal display 3', the operation table 5, the arm rest 6, the coin insertion slot 9, the bill insertion slot 10, the coin payout slot 15, the coin receiving portion 16, the machine front face panel 20, a lower liquid crystal display 501, a control bar 502, a protection panel 503, an adjustment mechanism 511 and an attachment angle display region 601.

The upper liquid crystal display 3' is provided at the upper part of the front face of the cabinet 2 and has a credit display frame 3A for displaying the number of credits stored in the RAM 52. The lower liquid crystal display 501 is provided in the interior of a center part of the cabinet 2 and has the variable display portions 21, 22, 23, 24, 25 and the attachment angle display region 601.

The control bar 502 is provided at the arm rest 6. A player can grip the control bar 502 to move the lower liquid crystal display 501, thereby automatically adjusting an inclination (attachment angle) of the lower liquid crystal display 501 with respect to the cabinet 2 in a stepwise manner. The control bar 502 is attached with an operation switch 504. When the control bar 502 is moved, the operation switch 504 outputs an operation signal to the CPU 50 via an operation circuit 505 (see FIG. 28). The protection panel 503 is provided at the center part of the machine front face panel 20 to protect the lower liquid crystal display 501.

Figure 26:
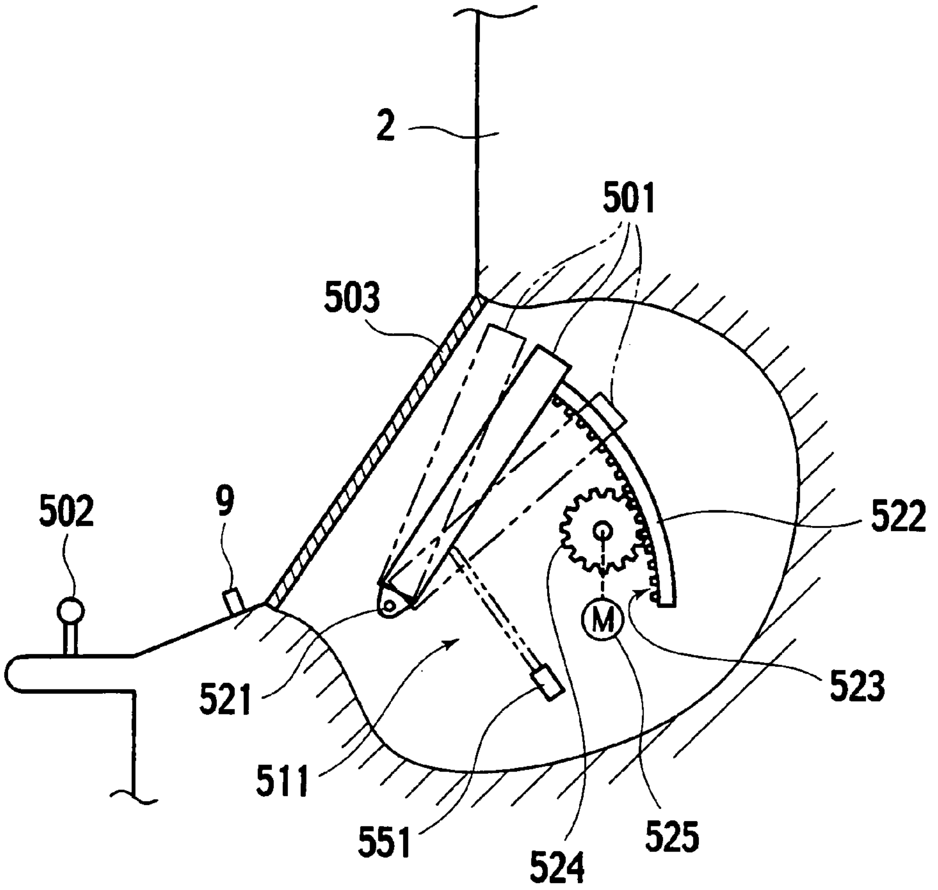
FIG. 26 is a schematic side view of an adjusting mechanism in the second embodiment of the present invention.

As shown in FIG. 26, the adjustment mechanism 511 comprises a rotation axis 521, a rack 522, a pinion 524, a stepping motor 525 and an attachment angle sensor 551. The rotation axis 521 is supported to the machine front face panel 20. The lower part of the lower liquid crystal display 501 is supported to the cabinet 2 via the rotation axis 521 in a rotatable manner. The rack 522 is formed in a circular arc-like shape and is provided in the cabinet 2. The rack 522 is fixed at an upper part of the lower liquid crystal display 501 so as to be opposed to the protection panel 503. The pinion 524 is supported to the cabinet 2 and is engaged with a tooth plane 523 of the rack 522. The stepping motor 525 is mounted in the cabinet 2 to rotate the pinion 524. The stepping motor 525 receives a step signal from the CPU 50 via a motor driving circuit 532 (see FIG. 28). The attachment angle sensor 551 is mounted in the cabinet 2 to measure the inclination of the lower liquid crystal display 501 with respect to the cabinet 2 and output a measurement signal to the CPU 50 when detecting that the attachment angle reaches a limit angle (see FIG. 28).

Figure 27:
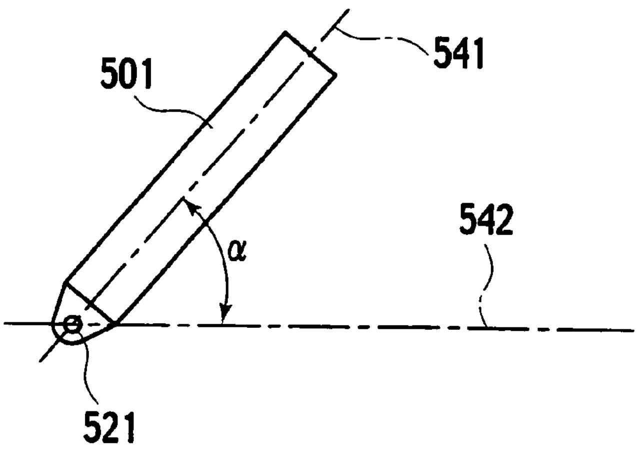
FIG. 27 is an expanded schematic side view of the adjustment mechanism when an attachment angle of a lower liquid crystal display is αdegrees in the second embodiment of the present invention.
Figure 28:
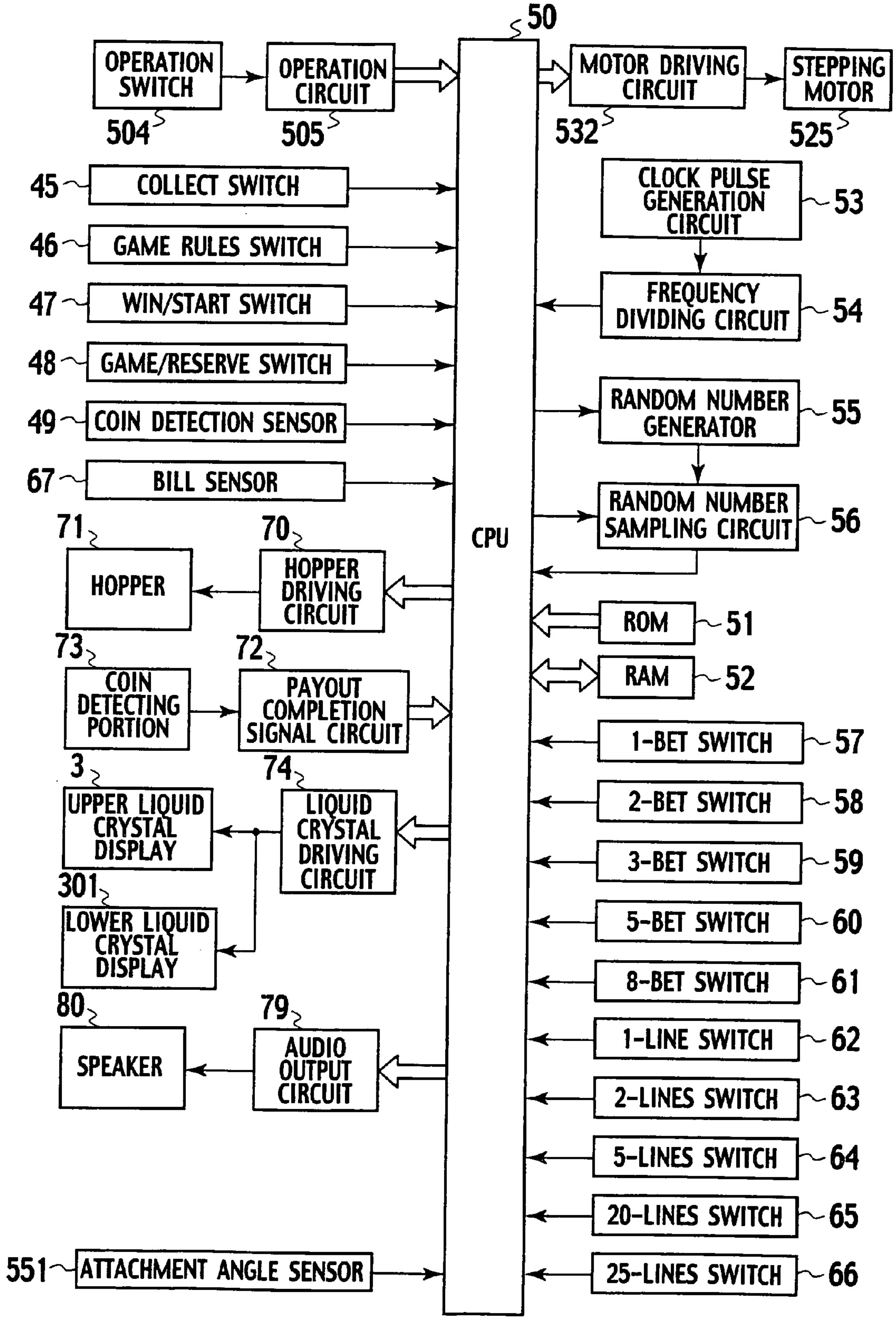
FIG. 28 is a control block diagram of the slot machine in the second embodiment of the present invention.

It is noted that, as shown in FIG. 27, an angle a formed by the intersection of a center line 541 of the lower liquid crystal display 501 with a horizontal line 542 passing above the rotation axis 521 is defined as the inclination (attachment angle) of the lower liquid crystal display 501 with respect to the cabinet 2.

Next, the operation of the adjustment mechanism 511 will be described.

When a player moves the control bar 502, the operation signal is inputted from the operation switch 504 to the CPU 50 via the operation circuit 505. When the CPU 50 receives the operation signal, the CPU 50 outputs the step signal to the stepping motor 525 via the motor driving circuit 532. When the stepping motor 525 receives the step signal, the stepping motor 525 rotates the pinion 524 by a predetermined angle. The rotation of the pinion 524 adjusts the attachment angle of the lower liquid crystal display 501 via the rack 522.

When the player continues to push the control bar 502, the step motor 525 rotates the pinion 524 in a clockwise direction to slant the lower liquid crystal display 501 with respect to the cabinet 2 in a stepwise manner. Then, when the control bar 502 is returned to an original position (home position), the step motor 525 stops the pinion 524 to fix the attachment angle of the lower liquid crystal display 501.

On the other hand, when the player continues to pull the control bar 502, the step motor 525 rotates the pinion 524 in a counter-clockwise direction to raise the lower liquid crystal display 501 with respect to the cabinet 2. Then, when the control bar 502 is returned to the original position (home position), the step motor 525 stops the pinion 524 to fix the attachment angle of the lower liquid crystal display 501.

The attachment angle sensor 551 measures the attachment angle of the lower liquid crystal display 501 at a fixed cycle. When the attachment angle sensor 551 detects that the attachment angle reaches the limit angle, the attachment angle sensor 551 outputs the measurement signal to the CPU 50. When the CPU 50 receives the measurement signal, the CPU 50 stops the stepping motor 525 via the motor driving circuit 532. In this manner, the adjustment mechanism 511 prevents an excessive load from being applied on the lower liquid crystal display 501, the rack 522 and the pinion 524.

The attachment angle display region 601 displays the attachment angle of the lower liquid crystal display 301 measured by the attachment angle sensor 551.

Next, a main processing program of the slot machine 1' will be described. The main processing program of the slot machine 1' is identical with the main processing program of the slot machine 1 except the start reception processing and the safety processing. Here, only the start reception processing performed by Step S11 of the main processing program will be described in detail.

Figure 29:
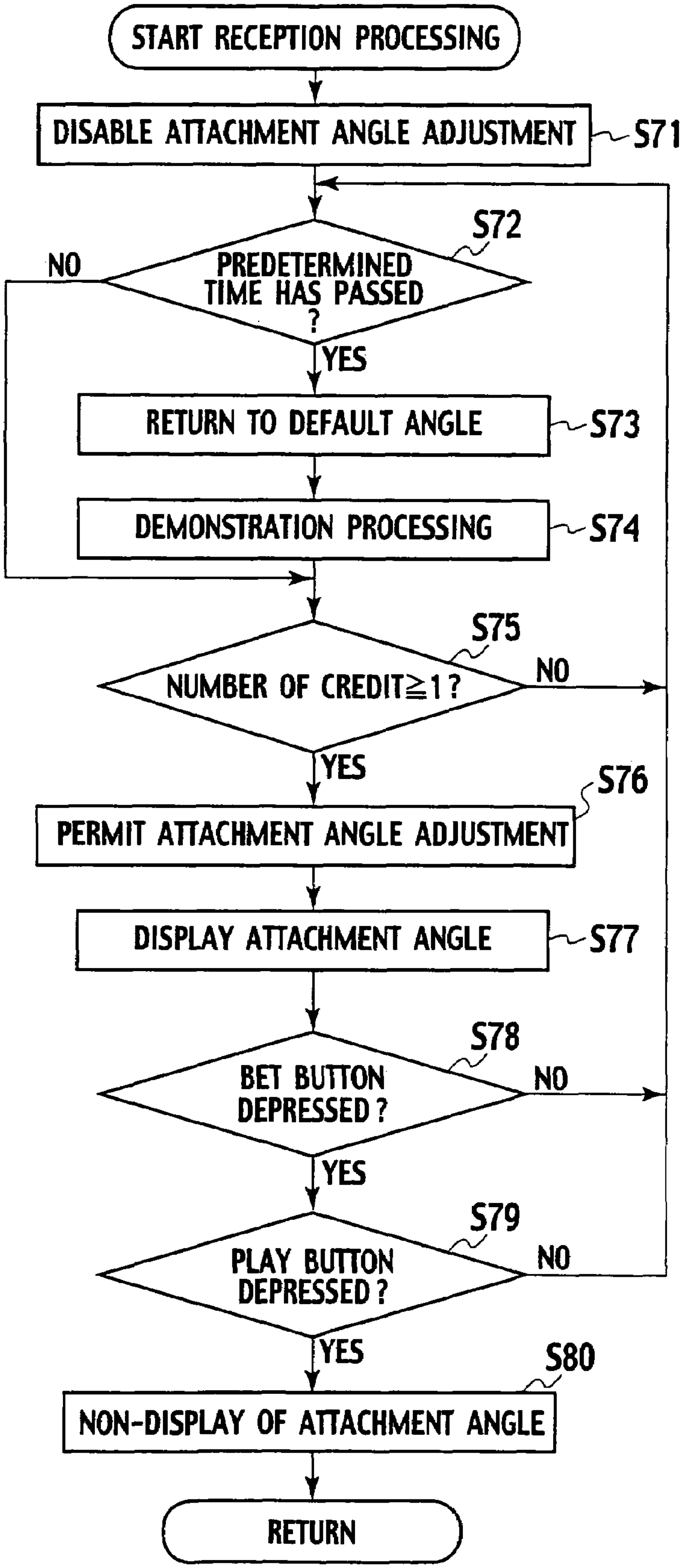
FIG. 29 is a flowchart of a start reception processing program in the second embodiment of the present invention.

As shown in FIG. 29, Step S71 allows the CPU 50 to perform a processing for disabling an attachment angle adjustment. This processing causes the CPU 50 to ignore the operation signal from the operation switch 504 and not to output the driving signal to the motor driving circuit 532. Alternatively, this processing causes the CPU 50 to output a driving signal to the motor driving circuit 532 not to move the stepping motor 525. In this status, even when the player operates the control bar 502, the stepping motor 525 is not rotated. Therefore, the player cannot adjust the attachment angle of the lower liquid crystal display 501.

Step S72 allows the CPU 50 to determine whether a predetermined time (e.g., 15 seconds) has passed or not. When the predetermined time has not passed (Step S72: NO), the CPU 50 proceeds to Step S75. When the predetermined time has passed (Step S72: YES), the CPU 50 proceeds to Step S73 to return the attachment angle of the lower liquid crystal display 501 to the default angle. More specifically, the CPU 50 allows the motor driving circuit 532 to rotate the motor 525 through a feedback control while the CPU 50 causes the attachment angle sensor 551 to measure the attachment angle of the lower liquid crystal display 301, thereby returning the attachment angle of the lower liquid crystal display 501 to the default angle.

Step S74 allows the upper liquid crystal display 3, or the lower liquid crystal display 501 to display a demonstration image.

Step S75 allows the CPU 50 to determine whether the number of credits stored in the RAM 52 is equal to or higher than "1" or not. When the number of credit is smaller than "1" (Step S75: No), the CPU 50 returns to Step S72. When the number of credits is equal to or higher than "1" (Step S75: YES), the CPU 50 proceeds to Step S76.

Step S76 allows the CPU 50 (permission means) to perform a processing for permitting an attachment angle adjustment. When this processing is performed, the CPU 50 receives the operation signal from the operation switch 504 to calculate a rotation amount and a rotation direction of the stepping motor 525, based on the operation signal from the operation switch 504. Then, the CPU 50 outputs to the motor driving circuit 532 a driving signal for moving the stepping motor 525 with the calculated rotation amount and rotation direction. In this status, when the player operates the control bar 502, the stepping motor 525 is rotated to adjust the attachment angle of the lower liquid crystal display 501.

Step S77 allows the CPU 50 (display control means) to use the attachment angle sensor 551 to measure the attachment angle of the lower liquid crystal display 501. Then, the measured attachment angle value is displayed in display region 601.

Step S78 allows the CPU 50 to determine whether the operation of the BET1 PER LINE button 33, the operation of the BET2 PER LINE button 34, the operation of the BET3 PER LINE button 35, the operation of the BET5 PER LINE button 36 or the operation of the BET8 PER LINE button 37 is performed or not. When the operation of the BET1 PER LINE button 33, the operation of the BET2 PER LINE button 34, the operation of the BET3 PER LINE button 35, the operation of the BET5 PER LINE button 36 or the operation of the BET8 PER LINE button 37 is not performed (Step S78: NO), the CPU 50 returns to Step S72. When the operation of the BET1 PER LINE button 33, the operation of the BET2 PER LINE button 34, the operation of the BET3 PER LINE button 35, the operation of the BET5 PER LINE button 36 or the operation of the BET8 PER LINE button 37 is performed (S27: YES), the CPU 50 proceeds to Step S79. It is noted that the CPU 50 also may determine the above processing based on other input signals regardless the operation signal.

Step S79 allows the CPU 50 to determine whether the operation of the RED PLAY1 LINE button 39, the operation of the RED PLAY2 LINES button 40, the operation of the RED PLAY5 LINES button 41, the operation of the RED PLAY20 LINES button 42 or the operation of the BLACK PLAY25 LINES button 43 is performed or not. When the operation of the RED PLAY1 LINE button 39, the operation of the RED PLAY2 LINES button 40, the operation of the RED PLAY5 LINES button 41, the operation of the RED PLAY20 LINES button 42 or the operation of the BLACK PLAY25 LINES button 43 is not performed (Step S79: NO), the CPU 50 returns to Step S72. When the operation of the RED PLAY1 LINE button 39, the operation of the RED PLAY2 LINES button 40, the operation of the RED PLAY5 LINES button 41, the operation of the RED PLAY20 LINES button 42 or the operation of the BLACK PLAY25 LINES button 43 is performed (Step S79: YES), the CPU 50 proceeds to Step S80.

Step S80 allows the CPU 50 to delete the display in the attachment angle display region 601. Then, the attachment angle display region 601 itself is also deleted from the lower liquid crystal display 501. Thus, the attachment angle display region 601 is not recognized from outside.

Next, a modification of this embodiment will be described.

The attachment angle of the lower liquid crystal display 301 is directly measured by an attachment angle sensor 551. Thus, the CPU 50 uses the motor driving circuit 532 to rotate the stepping motor 525 while the CPU 50 uses the attachment angle sensor 551 to detect the attachment angle of the lower liquid crystal display 501 (feedback control), thereby the attachment angle is returned to the default angle. The CPU 50 performs the feedback control based on the control program and control data stored in the ROM 51. Furthermore, the motor driving circuit 532 manages a rotation position of the stepping motor 525. Therefore, CPU 50 also may control the rotation position of the stepping motor 525 through a feed forward control to return the attachment angle to the default angle.

What is claimed is:

1. A gaming machine comprising:

a cabinet;

a display apparatus attached to the cabinet;

an adjustment unit configured to adjust an attachment angle of the display apparatus with respect to the cabinet, in accordance with a movement of the display apparatus; and a liquid storage unit having liquid and a plurality of inclination indicators and configured to present the attachment angle based on a relative positional relation between the liquid and the inclination indicators the liquid storage unit being made of columnar transparent plastic which has a hollow part therein, and wherein the plurality of inclination indicators comprise:

a first inclination indicator provided at circular side faces and an annular side face of the liquid storage unit; and a plurality of second inclination indicators provided at the annular side face of the liquid storage unit, the second inclination indicators being formed in a circumferential direction of a center of the liquid storage unit, around the first inclination indicator.

2. The gaming machine according to claim 1, wherein a level of the liquid overlaps with the first inclination indicator when the attachment angle is a predetermined angle.

3. The gaming machine according to claim 1, wherein a level of the liquid is parallel with the first inclination indicator and the second inclination indicators on the annular side face of the liquid storage unit.

4. The gaming machine according to claim 1, wherein the liquid is a fluorescent color.

5. A gaming machine comprising:

a cabinet;

a display apparatus attached to the cabinet;

an adjustment unit configured to adjust an attachment angle of the display apparatus with respect to the cabinet, in accordance with a movement of the display apparatus; and a liquid storage unit having liquid and a plurality of inclination indicators and configured to present the attachment angle based on a relative positional relation between the liquid and the inclination indicators the liquid storage unit being made of prismatic transparent plastic having a hollow part therein, and wherein the plurality of inclination indicators comprise:

a first inclination indicator provided at four adjacent faces of the liquid storage unit; and a plurality of second inclination indicators provided at one face of the four adjacent faces of the liquid storage unit, the second inclination indicators being formed in upper and lower directions of a center of the liquid storage unit, around the first inclination indicator.

6. The gaming machine according to claim 5, wherein a level of the liquid overlaps with the first inclination indicator when the attachment angle is a predetermined angle.

7. The gaming machine according to claim 5, wherein a level of the liquid is parallel with the first inclination indicator and the second inclination indicators on the one face of the liquid storage unit.

8. A gaming machine comprising:

a cabinet;

a display apparatus attached to the cabinet;

an adjustment unit configured to adjust an attachment angle of the display apparatus with respect to the cabi net, in accordance with a movement of the display apparatus; and a liquid storage unit having liquid and a plurality of inclination indicators and configured to present the attachment angle based on a relative positional relation between the liquid and the inclination indicators, the liquid storage unit being fixed to a shaft extending from the display apparatus and is positioned at a side face of the cabinet.

9. A gaming machine comprising:

a cabinet;

a display apparatus attached to the cabinet;

an adjustment unit configured to adjust an attachment angle of the display apparatus with respect to the cabinet, in accordance with a movement of the display apparatus; and a liquid storage unit having liquid and a plurality of inclination indicators and configured to present the attachment angle based on a relative positional relation between the liquid and the inclination indicators, the liquid storage unit being fixed to a shaft extending from the display apparatus and is positioned at an end portion of the display apparatus.

* * * * *